US006977178B2

(12) United States Patent
Hodge et al.

(10) Patent No.: US 6,977,178 B2
(45) Date of Patent: Dec. 20, 2005

(54) SYSTEM AND METHOD FOR TRANSGENIC AND TARGETED MUTAGENESIS SCREENING

(75) Inventors: Timothy A. Hodge, Cordova, TN (US); Shawn O'Malley, Milleville, MA (US)

(73) Assignee: TransnetYX, Inc., Cordova, TN (US)

( * ) Notice: Subject to any disclaimer, the term of this patent is extended or adjusted under 35 U.S.C. 154(b) by 0 days.

(21) Appl. No.: 10/233,942

(22) Filed: Sep. 3, 2002

(65) Prior Publication Data

US 2003/0165922 A1 Sep. 4, 2003

(Under 37 CFR 1.47)

Related U.S. Application Data

(63) Continuation of application No. 09/945,952, filed on Sep. 4, 2001.
(60) Provisional application No. 60/230,371, filed on Sep. 6, 2000.

(51) Int. Cl.⁷ .......................... G01N 33/00; C12Q 1/68; C12N 1/08; C07H 21/02
(52) U.S. Cl. ........................ 436/94; 435/6; 435/270; 435/287.2; 436/172; 436/800; 436/805; 536/23.1; 536/24.31
(58) Field of Search .................. 435/6, 183, 91.1, 435/287.2; 436/94; 536/23.1, 24.31

(56) References Cited

U.S. PATENT DOCUMENTS

| 4,554,088 A | 11/1985 | Whitehead et al. ....... 252/62.54 |
| 4,628,037 A | 12/1986 | Chagnon et al. ............ 436/526 |
| 4,672,040 A | 6/1987 | Josephson .................... 436/526 |
| 4,695,393 A | 9/1987 | Whitehead et al. ....... 252/62.54 |
| 4,698,302 A | 10/1987 | Whitehead et al. ........... 435/94 |
| 4,920,213 A | 4/1990 | Dale et al. ................ 536/23.72 |
| 5,139,744 A | 8/1992 | Kowalski ...................... 422/67 |
| 5,182,203 A | 1/1993 | Ebersole et al. ............ 435/196 |
| 5,196,306 A | 3/1993 | Bobrow et al. .............. 435/7.9 |
| 5,355,304 A | 10/1994 | DeMoranville et al. ..... 364/413 |
| 5,366,896 A | 11/1994 | Margrey et al. .............. 436/48 |
| 5,413,923 A | 5/1995 | Kucherlapati et al. ...... 435/463 |
| 5,427,910 A * | 6/1995 | Kamentsky et al. ........... 435/6 |
| 5,489,513 A | 2/1996 | Springer et al. ............... 435/6 |
| 5,527,685 A | 6/1996 | Hodges et al. ........... 435/172.3 |
| 5,527,695 A | 6/1996 | Hodges et al. ........... 435/172.3 |
| 5,582,989 A | 12/1996 | Caskey et al. .................. 435/6 |
| 5,583,001 A | 12/1996 | Bobrow et al. .............. 435/7.5 |
| 5,596,089 A | 1/1997 | Silversides et al. ........ 536/24.3 |
| 5,596,092 A | 1/1997 | Schneider ................... 536/25.4 |
| 5,631,844 A | 5/1997 | Margret et al. ............. 364/496 |
| 5,654,182 A | 8/1997 | Wahl et al. ................ 435/172.1 |
| 5,656,493 A | 8/1997 | Mullis et al. ............... 435/286.1 |
| 5,658,548 A | 8/1997 | Padhye et al. .............. 423/335 |
| 5,658,744 A * | 8/1997 | Ochoa et al. ............. 435/7.24 |
| 5,665,549 A | 9/1997 | Pinkel et al. .................. 435/6 |
| 5,677,177 A | 10/1997 | Wahl et al. .................. 435/325 |
| 5,705,628 A | 1/1998 | Hawkins .................... 536/25.4 |
| 5,720,936 A | 2/1998 | Wadsworth et al. ......... 424/9.1 |
| 5,721,098 A | 2/1998 | Pinkel et al. .................. 435/6 |
| 5,731,095 A | 3/1998 | Milco et al. ................ 428/482 |
| 5,731,158 A | 3/1998 | Bobrow et al. .............. 435/7.5 |
| 5,733,753 A | 3/1998 | Jorgensen .................. 435/91.4 |
| 5,804,382 A | 9/1998 | Sytkowski et al. ............. 435/6 |
| 5,837,466 A | 11/1998 | Lane et al. ..................... 435/6 |
| 5,841,975 A | 11/1998 | Layne et al. ............. 395/200.3 |
| 5,858,658 A | 1/1999 | Haemmerle et al. ........... 435/6 |
| 5,864,020 A * | 1/1999 | Bennett et al. ........ 530/388.24 |
| 5,888,723 A | 3/1999 | Sutton et al. .................. 435/5 |
| 5,898,071 A | 4/1999 | Hawkins .................... 536/25.4 |
| 5,932,780 A | 8/1999 | Soreq et al. .................. 800/13 |
| 5,942,402 A | 8/1999 | Schmidt et al. ................ 435/6 |
| 5,968,731 A | 10/1999 | Layne et al. ................... 435/5 |
| 5,973,138 A | 10/1999 | Collis ......................... 536/25.4 |
| 6,027,945 A | 2/2000 | Smith et al. ................ 436/526 |
| 6,037,465 A | 3/2000 | Hillebrand et al. ...... 536/24.42 |
| 6,043,039 A | 3/2000 | Bar-Am et al. ................ 435/6 |
| 6,046,038 A * | 4/2000 | Nilsen ....................... 435/91.1 |

(Continued)

FOREIGN PATENT DOCUMENTS

| EP | 133286 A1 | 9/2001 |
| WO | WO 91/12079 | 8/1991 |
| WO | WO 93/25709 | 12/1993 |
| WO | WO 94/11838 | 5/1994 |
| WO | WO 96/5488 | 2/1996 |
| WO | WO 99/02667 | 7/1998 |
| WO | WO98/39475 | 9/1998 |
| WO | WO 00/40593 | 1/2000 |

OTHER PUBLICATIONS

Levison et al., "Recent developments of magnetic beads for use in nucleic acid purification," Journal of Chromatography A, 816 (1998) 107–111.*

Charles River Genetic Testing Services Order Form.

Hayes et al., M.D. Computing: Computers in Medical Practice, Jul.–Aug. 1996 13(4): 330–334; abstract only.

A. Diagger & Co. Catalog, 1999, pp. 528, 542, 543.

Primary Examiner—Bradley L. Sisson
(74) Attorney, Agent, or Firm—Butler, Snow, O'Mara Stevens & Canada PLLC

(57) ABSTRACT

The present invention provides a method and apparatus for to conduct transgenic and targeted mutagenesis screening of genomic DNA. This invention also provides a system for screening DNA for a designated genetic sequence. The system includes a computer having a processor, memory and web browser, wherein the computer receives instructions concerning the designated genetic sequence and other screening parameter selection from a remote user via a form of electronic communication, and an automatic screening device that analyzes samples of genomic DNA for the designated sequence.

7 Claims, 13 Drawing Sheets

U.S. PATENT DOCUMENTS

| | | | | |
|---|---|---|---|---|
| 6,054,266 | A | 4/2000 | Kronick et al. | 435/6 |
| 6,054,270 | A | 4/2000 | Southern | 435/6 |
| 6,060,240 | A | 5/2000 | Kamb et al. | 435/6 |
| 6,078,902 | A | 6/2000 | Schenkler | 705/35 |
| 6,090,935 | A | 7/2000 | Breivik et al. | 436/25.4 |
| 6,107,032 | A | 8/2000 | Kilger et al. | 435/6 |
| 6,114,150 | A | 9/2000 | Weissman et al. | 435/91.2 |
| 6,117,635 | A | 9/2000 | Nazarenko et al. | 435/6 |
| 6,156,501 | A | 12/2000 | McGall et al. | 435/6 |
| 6,159,685 | A | 12/2000 | Pinkel et al. | 435/6 |
| 6,177,278 | B1 | 1/2001 | Haj-Ahman | 435/6 |
| 6,187,537 | B1 | 2/2001 | Zinn, Jr. et al. | 435/6 |
| 6,255,477 | B1 | 7/2001 | Kleiber et al. | 536/25.4 |
| 6,291,248 | B1 | 9/2001 | Haj-Ahman | 436/94 |
| 6,355,792 | B1 | 3/2002 | Michaelson et al. | 536/25.4 |
| 6,368,800 | B1 | 4/2002 | Smith et al. | 435/6 |
| 6,376,194 | B2 | 4/2002 | Smith et al. | 435/6 |
| 6,465,178 | B2 | 10/2002 | Chappa et al. | 435/6 |
| 6,480,791 | B1 | 11/2002 | Strathmann | 702/20 |
| 6,548,253 | B1 | 4/2003 | Holschub et al. | 536/22.1 |
| 6,699,987 | B2 | 3/2004 | Hillebrand et al. | 536/25.4 |
| 2002/0012934 | A1 | 1/2002 | Meshen et al. | 435/6 |
| 2002/0177137 | A1 | 11/2002 | Hodge | 435/6 |
| 2003/0082605 | A1 | 5/2003 | Hodge | 435/6 |
| 2003/0087286 | A1 | 5/2003 | Hodge | 435/6 |
| 2003/0165922 | A1 | 9/2003 | Hodge et al. | 435/91.2 |
| 2003/0207289 | A1 | 11/2003 | Hodge et al. | 435/6 |
| 2003/0207295 | A1 | 11/2003 | Gunderson et al. | 435/6 |

OTHER PUBLICATIONS

Research Genetics (advertisement), Nucleic Acids Research, Aug. 1994, 22(5).

Masayuki Egashira, et al., "Visible Integration of the Adenosine Deaminase (ADA) Gene into the Recipient Genome After Gene Therapy," American Journal of Medical Genetics 75:314–317 (1998).

Peijung Zhang, et al., "Gene Transfer, Expression and Inheritance of pRSV–Rainbow Trout–GH cDNA in the Common Carp, Cyprinus carpio (Linnaeous)," Molecular Reproduction and Development 25:3–13 (1990).

Kenneth E. Drazen, et al., "Viral IL–10 Gene Therapy Inhibits TNF–a and IL–10, Not IL–6, In the Newborn Endotoxemic Mouse," Journal of Pediatric Surgery, vol. 31, No. 3 (Mar.), 1996; pp 411–414.

Nancy Shui–Fong Ma, et al., "Owl Monkey Gene Map: Evidence for a Homologous Human Chromosome 7q Region near the Cystic Fibrosis Locus," Genomics 5, 389–396 (1989).

Zoe A. Weaver, et al., "A Recurring Pattern of Chromosomal Aberrations in Mammary Gland Tumors of MMTV–cmyc Transgenic Mice," Genes, Chromosomes & Cancer, 25:251–260 (1999).

Ping Fu, et al., "Rapid Determination of Transgene Copy Number in Stably–Transfected Mammalian Cells by Competitive PCR," Journal of Biochemical and Biophysical Methods 40, 101–112 (1999).

"New Strategies for Gene Knockout," Chapter 17, Methods in Gene Biotechnology, pp. 339–365.

* cited by examiner

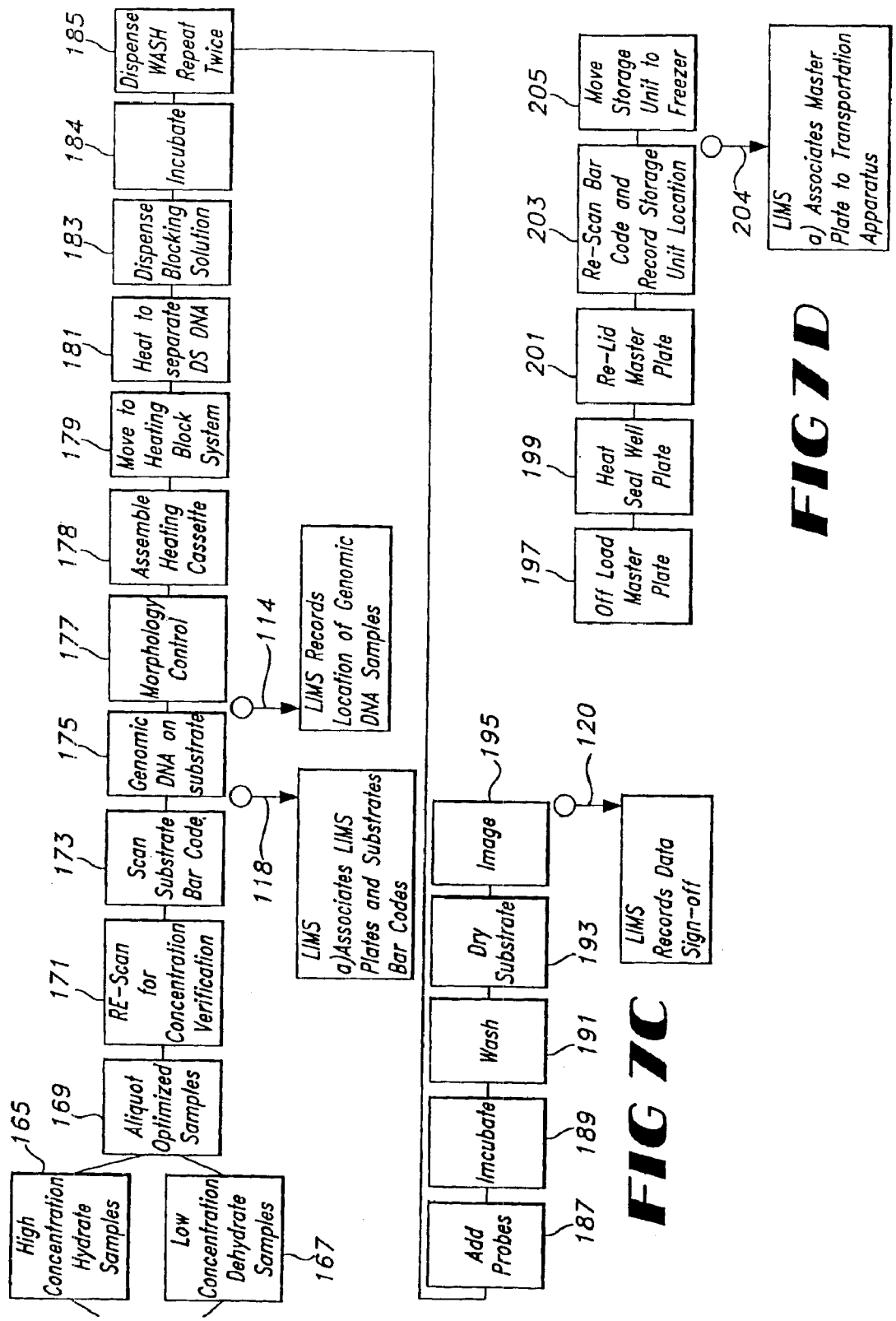

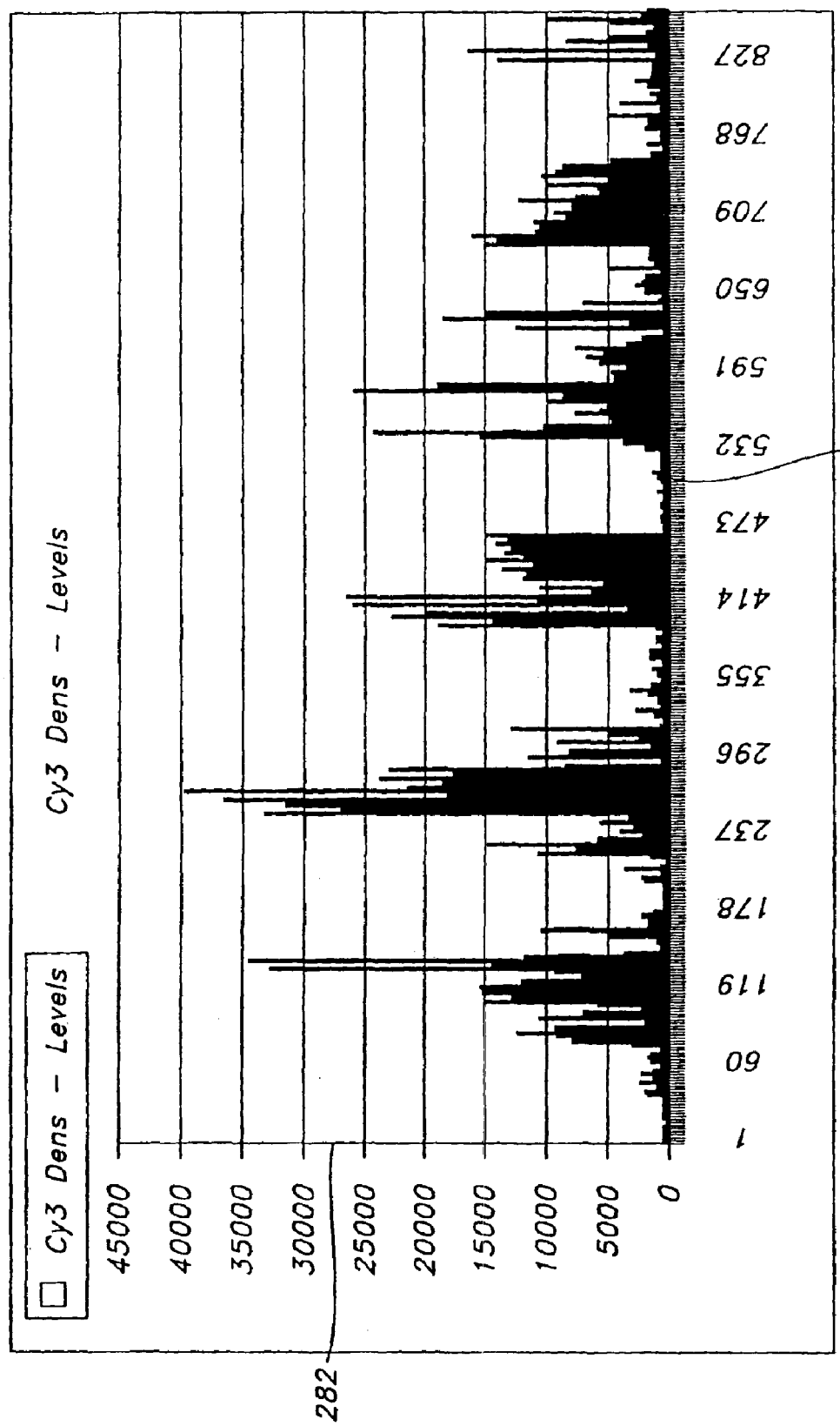

SEQUENCE LISTING

<160> NUMBER OF SEQ ID NOS: 40

<210> SEQ ID NO 1
<211> LENGTH: 795
<212> TYPE: DNA
<213> ORGANISM: Streptomyces fradiae

<400> SEQUENCE: 1

| | | | | | |
|---|---|---|---|---|---|
| atgattgaac | aagatggatt | gcacgcaggt | tctccggccg | cttgggtgga | gaggctattc | 60 |
| ggctatgact | gggcacaaca | gacaatcggc | tgctctgatg | ccgccgtgtt | ccggctgtca | 120 |
| gcgcagggc | gcccggttct | ttttgtcaag | accgacctgt | ccggtgccct | gaatgaactg | 180 |
| caggacgagg | cagcgcggct | atcgtggctg | gccacgacgg | gcgttccttg | cgcagctgtg | 240 |
| ctcgacgttg | tcactgaagc | gggaagggac | tggctgctat | gggcgaagt | gccggggcag | 300 |
| gatctcctgt | catctcacct | tgctcctgcc | gagaaagtat | ccatcatggc | tgatgcaatg | 360 |
| cggcggctgc | atacgcttga | tccggctacc | tgcccattcg | accaccaagc | gaaacatcgc | 420 |
| atcgagcgag | cacgtactcg | gatggaagcc | ggtcttgtcg | atcaggatga | tctggacgaa | 480 |
| gagcatcagg | ggctcgcgcc | agccgaactg | ttcgccaggc | tcaaggcgcg | catgcccgac | 540 |
| ggcgaggatc | tcgtcgtgac | ccatggcgat | gcctgcttgc | cgaatatcat | ggtggaaaat | 600 |
| ggccgctttt | ctggattcat | cgactgtggc | cggctgggtg | tggcggaccg | ctatcaggac | 660 |
| atagcgttgg | ctacccgtga | tattgctgaa | gagcttggcg | gcgaatgggc | tgaccgcttc | 720 |
| ctcgtgcttt | acggtatcgc | cgctcccgat | tcgcagcgca | tcgccttcta | tcgccttctt | 780 |
| gacgagttct | tctga | | | | | 795 |

<210> SEQ ID NO 2
<211> LENGTH: 1026
<212> TYPE: DNA
<213> ORGANISM: Streptomyces hygroscopicus

<400> SEQUENCE: 2

| | | | | | |
|---|---|---|---|---|---|
| atgaaaaagc | ctgaactcac | cgcgacgtct | gtcgagaagt | ttctgatcga | aaagttcgac | 60 |
| agcgtctccg | acctgatgca | gctctcggag | ggcgaagaat | ctcgtgcttt | cagcttcgat | 120 |
| gtaggagggc | gtggatatgt | cctgcgggta | aatagctgcg | ccgatggttt | ctacaaagat | 180 |
| cgttatgttt | atcggcactt | tgcatcggcc | gcgctcccga | ttccggaagt | gcttgacatt | 240 |
| ggggaattca | gcgagagcct | gacctattgc | atctcccgcc | gtgcacaggg | tgtcacgttg | 300 |
| caagacctgc | ctgaaaccga | actgcccgct | gttctgcagc | cggtcgcgga | ggccatggat | 360 |
| gcgatcgctg | cggccgatct | tagccagacg | agcgggttcg | gcccattcgg | accgcaagga | 420 |
| atcggtcaat | acactacatg | gcgtgatttc | atatgcgcga | ttgctgatcc | ccatgtgtat | 480 |
| cactggcaaa | ctgtgatgga | cgacaccgtc | agtgcgtccg | tcgcgcaggc | tctcgatgag | 540 |
| ctgatgcttt | gggccgagga | ctgccccgaa | gtccggcacc | tcgtgcacgc | ggatttcggc | 600 |
| tccaacaatg | tcctgacgga | caatggccgc | ataacagcgg | tcattgactg | gagcgaggcg | 660 |
| atgttcgggg | attcccaata | cgaggtcgcc | aacatcttct | tctggaggcc | gtggttggct | 720 |
| tgtatggagc | agcagacgcg | ctacttcgag | cggaggcatc | cggagcttgc | aggatcgccg | 780 |
| cggctccggg | cgtatatgct | ccgcattggt | cttgaccaac | tctatcagag | cttggttgac | 840 |
| ggcaatttcg | atgatgcagc | ttgggcgcag | ggtcgatgcg | acgcaatcgt | ccgatccgga | 900 |
| gccgggactg | tcgggcgtac | acaaatcgcc | cgcagaagcg | cggccgtctg | gaccgatggc | 960 |

```
tgtgtagaag tactcgccga tagtggaaac cgacgcccca gcactcgtcc gagggcaaag    1020
gaatag                                                               1026

<210> SEQ ID NO 3
<211> LENGTH: 600
<212> TYPE: DNA
<213> ORGANISM: streptomyces alboniger

<400> SEQUENCE: 3
atgaccgagt acaagcccac ggtgcgcctc gccacccgcg acgacgtccc ccgggccgta      60
cgcaccctcg ccgccgcgtt cgccgactac cccgccacgc gccacaccgt cgacccggac    120
cgccacatcg agcgggtcac cgagctgcaa gaactcttcc tcacgcgcgt cgggctcgac    180
atcggcaagg tgtgggtcgc ggacgacggc gccgcggtgg cggtctggac cacgccggag    240
agcgtcgaag cggggggcgg tgttcgccga gatcggcccgc gcatggccga gttgagcggt    300
tcccggctgg ccgcgcagca acagatggaa ggcctcctgg cgccgcaccg gcccaaggag    360
cccgcgtggt tcctggccac cgtcggcgtc tcgcccgacc accagggcaa gggtctgggc    420
agcgccgtcg tgctccccgg agtggaggcg gccgagcgcg ccggggtgcc cgccttcctg    480
gagacctccg cgccccgcaa cctcccttc tacgagcggc tcggcttcac cgtcaccgcc    540
gacgtcgagt gcccgaagga ccgcgcgacc tggtgcatga cccgcaagcc cggtgcctga    600

<210> SEQ ID NO 4
<211> LENGTH: 34
<212> TYPE: DNA
<213> ORGANISM: artificial sequence
<220> FEATURE:
<223> OTHER INFORMATION: Artificial recombinant mutation as described
      in U.S Patent Nos. 5,654,182 and 5,677,177

<400> SEQUENCE: 4
ataacttcgt ataatgtatg ctatacgaag ttat                                 34

<210> SEQ ID NO 5
<211> LENGTH: 96
<212> TYPE: DNA
<213> ORGANISM: artificial sequence
<220> FEATURE:
<223> OTHER INFORMATION: Artificial recombinant mutation as described
      in U.S. Patent No. 5,527,695

<400> SEQUENCE: 5
gaagttccta tactttctag agaataggaa cttccgaata ggaacttcct tcaaggatat      60
gaaagatctc ttatccttga aggcttatcc ttgaag                               96

<210> SEQ ID NO 6
<211> LENGTH: 20
<212> TYPE: DNA
<213> ORGANISM: Mus sp.

<400> SEQUENCE: 6
atcacaagta ctgggagagg                                                 20

<210> SEQ ID NO 7
<211> LENGTH: 20
<212> TYPE: DNA
<213> ORGANISM: Mus sp.

<400> SEQUENCE: 7
```
gtctcagagg ttaactcacc                                               20

<210> SEQ ID NO 8
<211> LENGTH: 20
<212> TYPE: DNA
<213> ORGANISM: Mus sp.

<400> SEQUENCE: 8
ttcttatctt cagccccacc                                               20

<210> SEQ ID NO 9
<211> LENGTH: 20
<212> TYPE: DNA
<213> ORGANISM: Mus sp.

<400> SEQUENCE: 9
ataacacggt gtgcaccacg                                               20

<210> SEQ ID NO 10
<211> LENGTH: 20
<212> TYPE: DNA
<213> ORGANISM: Mus sp.

<400> SEQUENCE: 10
tcccttcctg ttgactacag                                               20

<210> SEQ ID NO 11
<211> LENGTH: 20
<212> TYPE: DNA
<213> ORGANISM: Mus sp.

<400> SEQUENCE: 11
tacccacacg ggcttaaaac                                               20

<210> SEQ ID NO 12
<211> LENGTH: 20
<212> TYPE: DNA
<213> ORGANISM: Mus sp.

<400> SEQUENCE: 12
cactgccagt gtgttttcac                                               20

<210> SEQ ID NO 13
<211> LENGTH: 26
<212> TYPE: DNA
<213> ORGANISM: Mus sp.

<400> SEQUENCE: 13
ctgtgacgta tgatggattc aataca                                        26

<210> SEQ ID NO 14
<211> LENGTH: 26
<212> TYPE: DNA
<213> ORGANISM: Mus sp.

<400> SEQUENCE: 14
tcggccatag agctccatca gctgga                                        26

<210> SEQ ID NO 15
<211> LENGTH: 25
<212> TYPE: DNA
<213> ORGANISM: Mus sp.

<400> SEQUENCE: 15

-continued ctgtatggat aggaagggat gatgc                                          25

<210> SEQ ID NO 16
<211> LENGTH: 29
<212> TYPE: DNA
<213> ORGANISM: Mus sp.

<400> SEQUENCE: 16
ggctcaggcc attcttcatt ctcgggcct                                      29

<210> SEQ ID NO 17
<211> LENGTH: 31
<212> TYPE: DNA
<213> ORGANISM: artificial sequence
<220> FEATURE:
<223> OTHER INFORMATION: containing Mus plus sequence complimentary to
      an amplification molecule

<400> SEQUENCE: 17
ccggctgagt gacgcgcaga agacagggac g                                   31

<210> SEQ ID NO 18
<211> LENGTH: 31
<212> TYPE: DNA
<213> ORGANISM: artificial sequence
<220> FEATURE:
<223> OTHER INFORMATION: Mus plus sequence complimentary to a
      dendrite molecule

<400> SEQUENCE: 18
ggccgactca ctgcgcgtct tctgtcccgc c                                   31

<210> SEQ ID NO 19
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 19
ggccgactca ctgcgcgtct tctgtcccgc catcacaagt actgggagag g              51

<210> SEQ ID NO 20
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 20
ggccgactca ctgcgcgtct tctgtcccgc cgtctcagag gttaactcac c              51

<210> SEQ ID NO 21
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 21
ggccgactca ctgcgcgtct tctgtcccgc cttcttatct tcagccccac c              51

<210> SEQ ID NO 22
<211> LENGTH: 51
<212> TYPE: DNA

<213> ORGANISM: artificial sequence
<220> FEATURE:
<223> OTHER INFORMATION: Mus DNA plus DNA complimentary to a dendrite

<400> SEQUENCE: 22
ggccgactca ctgcgcgtct tctgtcccgc cataacacgg tgtgcaccac g      51

<210> SEQ ID NO 23
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 23
ggccgactca ctgcgcgtct tctgtcccgc ctcccttcct gttgactaca g      51

<210> SEQ ID NO 24
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 24
ggccgactca ctgcgcgtct tctgtcccgc ctacccacac gggcttaaaa c      51

<210> SEQ ID NO 25
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 25
ggccgactca ctgcgcgtct tctgtcccgc ccactgccag tgtgttttca c      51

<210> SEQ ID NO 26
<211> LENGTH: 57
<212> TYPE: DNA
<213> ORGANISM: artificial sequence
<220> FEATURE:
<223> OTHER INFORMATION: Mus DNA sequence plus DNA sequence
      complimentary to a dendrite

<400> SEQUENCE: 26
ggccgactca ctgcgcgtct tctgtcccgc cctgtgacgt atgatggatt caataca      57

<210> SEQ ID NO 27
<211> LENGTH: 57
<212> TYPE: DNA
<213> ORGANISM: artificial sequence
<220> FEATURE:
<223> OTHER INFORMATION: Mus DNA sequence plus DNA sequence
      complimentary to a dendrite

<400> SEQUENCE: 27
ggccgactca ctgcgcgtct tctgtcccgc ctcggccata gagctccatc agctgga      57

<210> SEQ ID NO 28
<211> LENGTH: 56
<212> TYPE: DNA
<213> ORGANISM: artificial sequence
<220> FEATURE:
<223> OTHER INFORMATION: Mus DNA sequence plus DNA sequence
      complimentary to a dendrite

```
<400> SEQUENCE: 28
ggccgactca ctgcgcgtct tctgtcccgc cctgtatgga taggaaggga tgatgc        56

<210> SEQ ID NO 29
<211> LENGTH: 60
<212> TYPE: DNA
<213> ORGANISM: artificial sequence
<220> FEATURE:
<223> OTHER INFORMATION: Mus DNA sequence plus DNA sequence
      complimentary to a dendrite

<400> SEQUENCE: 29
ggccgactca ctgcgcgtct tctgtcccgc cggctcaggc cattcttcat tctcgggcct    60

<210> SEQ ID NO 30
<211> LENGTH: 22
<212> TYPE: DNA
<213> ORGANISM: artificial sequence
<220> FEATURE:
<223> OTHER INFORMATION: Artificial DNA complimentary to Sequence
      "HUPPCA"

<400> SEQUENCE: 30
gcaaggacgc aaggaagcag ag                                             22

<210> SEQ ID NO 31
<211> LENGTH: 30
<212> TYPE: DNA
<213> ORGANISM: artificial sequence
<220> FEATURE:
<223> OTHER INFORMATION: Artificial DNA complimentary to a dendrite

<400> SEQUENCE: 31
ggccgactca ctgcgcgtct tctgtcccgc                                     30

<210> SEQ ID NO 32
<211> LENGTH: 52
<212> TYPE: DNA
<213> ORGANISM: artificial sequence
<220> FEATURE:
<223> OTHER INFORMATION: Artificial DNA plus DNA complimentary to
      "HUPPCA"

<400> SEQUENCE: 32
ggccgactca ctgcgcgtct tctgtcccgc gcaaggacgc aaggaagcag ag            52

<210> SEQ ID NO 33
<211> LENGTH: 51
<212> TYPE: DNA
<213> ORGANISM: artificial sequence
<220> FEATURE:
<223> OTHER INFORMATION: Mus plus DNA complimentary to a dendrite

<400> SEQUENCE: 33
ccggctgagt gacgcgcaga atcaagggcg cttcttatct tcagccccac c             51

<210> SEQ ID NO 34
<211> LENGTH: 20
<212> TYPE: DNA
<213> ORGANISM: Streptomyces hygroscopicus

<400> SEQUENCE: 34
caggatttgg gcaacatctt                                                20

<210> SEQ ID NO 35
```

```
<211> LENGTH: 51
<212> TYPE: DNA
<213> ORGANISM: artificial sequence
<220> FEATURE:
<223> OTHER INFORMATION: Mus DNA plus DNA complimentary to a dendrite

<400> SEQUENCE: 35
ccggctgagt gacgcgcaga atcaagggcg cttcttatct tcagccccac c          51

<210> SEQ ID NO 36
<211> LENGTH: 50
<212> TYPE: DNA
<213> ORGANISM: artificial sequence
<220> FEATURE:
<223> OTHER INFORMATION: Mus DNA plus DNA complimentary to a dendrite

<400> SEQUENCE: 36
ggccgactca ctgcgcgtct tctgtcccgc caggatttgg gcaacatctt            50

<210> SEQ ID NO 37
<211> LENGTH: 20
<212> TYPE: DNA
<213> ORGANISM: Mus sp.

<400> SEQUENCE: 37
atcacaagta ctgggagagg                                             20

<210> SEQ ID NO 38
<211> LENGTH: 20
<212> TYPE: DNA
<213> ORGANISM: Mus sp.

<400> SEQUENCE: 38
gtctcagagg ttaactcacc                                             20

<210> SEQ ID NO 39
<211> LENGTH: 20
<212> TYPE: DNA
<213> ORGANISM: Mus sp.

<400> SEQUENCE: 39
ttcttatctt cagccccacc                                             20

<210> SEQ ID NO 40
<211> LENGTH: 20
<212> TYPE: DNA
<213> ORGANISM: Mus sp.

<400> SEQUENCE: 40
ataacacggt gtgcaccacg                                             20
```

SYSTEM AND METHOD FOR TRANSGENIC AND TARGETED MUTAGENESIS SCREENING

CROSS-REFERENCED TO RELATED APPLICATIONS

This application is a continuation of Ser. No. 09/945,952, filed Sep. 4, 2001, which claims priority under U.S.C. §119(e), based on U.S. Provisional Application Ser. No. 60/230,371, filed Sep. 6, 2000. The entire disclosure of which is hereby incorporated by reference.

BACKGROUND OF THE INVENTION

1. Field of the Invention

This invention relates to a system for transgenic and targeted mutagenesis screening. Additionally, this invention relates to various methods to detect or screen for designated genetic sequences or portion thereof derived from a tissue sample. More specifically, this invention relates to a high volume apparatus for transgenic and targeted mutagenesis screening.

2. Description of the Related Art

Genomic modification resulting from mutations in the DNA of an organism can be transferred to the progeny if such mutations are present in the gametes of the organism, referred to as germ-line mutations. These mutations may arise from genetic manipulation of the DNA using recombinant DNA technology or may be introduced by challenging the DNA by chemical or physical means. DNA introduced via recombinant DNA technology can be derived from many sources, including but not limited to DNA from viruses, mycoplasm, bacteria, fungi, yeast, and chordates including mammals such as humans. Recombinant DNA technology allows for the introduction, deletion or replacement of DNA of an organism. Random introduction of DNA into a cell can be achieved by technologies such as transfection (including electroporation, lipofection), injection (pronuclear injection, nuclear transplantation) or transduction (viral infection). Random mutations (point mutations, deletions, amplifications) can be generated by treatment of cells with chemical mutagens or submitting them to physical insult such as X-irradiation or linear energy transfer irradiation (LET). Targeted addition, deletion or replacement of DNA in an organism (either inducible or non-inducible) is achieved via homologous recombination. Inducible systems employ sequence-specific recombinases such as Cre-LoxP (U.S. Pat. Nos. 5,654,182 and 5,677,177) and FLP/FRT (U.S. Pat. No. 5,527,695).

Transgenic organisms are organisms that carry DNA sequences (be it genes or gene segments) derived from another species, stably integrated into their genome. Transgenic mammals are generally created by microinjection of DNA into the pronucleus of fertilized eggs, a technique in which the number of DNA copies or the integration site of the DNA into the host genome is uncontrollable. A transgenic line refers to an organism that transmits the foreign DNA sequences to its offspring.

Targeted mutations, site directed mutagenesis or gene targeting is described as methods that employ homologous recombination of DNA to alter a specific DNA sequence within the host genome. This can result in inactivation of a gene (knock-out mutation), or genetic alteration of the gene (knock-in mutation). In mammals this can be achieved by transfection of a cloned, mutated gene segment (targeting construct) into embryonic stem cells (ES cells), which, via homologous recombination, replaces the endogenous gene segment in the ES cell. Animals derived from these ES cells will carry the targeted mutation in their genome. Further refinement of this technique involves inducible gene alteration, in which the endogenous gene has been targeted with a DNA segment that contains recognition sequences (LoxP or FRT sequences) for site-specific recombinases (Cre, FLP). Expression of the recombinase in the targeted ES cell or the ES cell-derived animal will result in deletion of the DNA segment flanked by the recognition sites. Depending on the configuration of targeting construct, this can result in inactivation, activation or alteration of the targeted gene. The advantage of an inducible system in animals is that the gene alteration can be induced at any point in time or in any tissue, depending on the ability to specifically activate the recombinase. This can be achieved by placing the recombinase under the control of inducible promoters (chemically or hormone-inducible promoters).

Transgenic and targeted mutagenesis screening is used to determine if a genome possesses specific genetic sequences that exist endogenously or have been modified, mutated or genetically engineered. Genomic DNA is screened for these modifications or mutations. Genomic DNA is challenging to sufficiently immobilize on the substrate because of its size. The genomic DNA includes both coding and non-coding regions. Therefore, the genomic DNA contains exons and introns, promoter and gene regulation regions, telomeres, origins or replication and non-functional intergenic DNA. The genomic DNA is a double stranded molecule which is methylated. Immobilizing cDNA and PCR amplicons differs in that the molecules are much smaller. Additionally, biochemical modification events, such as methylation, does not occur with the smaller molecules. Shena, M (2000) DNA Microarrrays: A Practical Approach. Oxford University Press, New York, N.Y.

Transgenic screening is currently done manually. The present manual system is time-consuming and can provide variable results depending on the laboratory and even depending on skill of laboratory workers. Presently, a researcher using southern blot technology may require greater than a week to screen a tissue sample for a transgene or a targeted mutation. In an alternative technology, up to thirty PCR (polymerase chain reaction) can be conducted in an Eppendorf microtube® (Brinkmann Instruments, Westbery, N.Y.) and separated on a gel. This process in most laboratories requires 3 to 7 days. A need exists in the industry to provide a system and method for more accurate, faster and high volume transgenic and targeted mutagenesis screening.

(8) BRIEF SUMMARY OF THE INVENTION

The present invention provides a unique solution to the above described problems by providing a method and system for automated transgenic and targeted mutagenesis testing.

The object of this invention is to provide higher volume screening of transgenic and targeted mutagenesis samples for a designated genetic sequence than by prior art methods. It is another object of this invention to provide screening results to a researcher more quickly than by prior art method to screen transgenic and targeted mutagenic samples. These objects are achieved by several features of this invention. These features include depositing prokaryotic or eukaryotic genomic DNA on a substrate and detecting the genomic DNA with a microarray imager to facilitate high volume screening. Additionally, an order process that provides a remote user's selection parameters to conduct screening of a sample and provides the associated reagents, in a coordinated way facilitates high volume screening of transgenic and targeted mutagenesis samples for a designated genetic sequence. In addition to this feature, screening of genomic DNA from cellular lysate using magnetic particles and lysing the tissue sample with a lysis buffer that is formulated to work while the samples are in transit to the screening laboratory from a remote user have been found to facilitate high volume screening. It should be noted that the techniques taught in the specification that enable higher volume screening of genomic DNA for a designated genetic sequence can be more broadly applied to by one skilled in the art to various methods to detect genetic sequences in samples of genomic DNA.

According to another aspect of this invention, a method to detect a designated genetic sequence in a sample of genomic DNA is provided. This method involves depositing the genomic DNA on a substrate; adding at least one labeled probe specific for a portion of the designated genetic sequence; and detecting the signal from at least one labeled probe specific for a portion of the designated genetic sequence to detect the designated genetic sequence in the sample of genomic DNA.

According to another aspect of this invention, a method to detect a designated genetic sequence in a sample of genomic DNA, by comparing the sample with a designated control sample of genomic DNA is provided. This method involves the steps of: depositing the genomic DNA from the sample at a first location on the substrate; depositing genomic DNA from the designated control sample at a second location on the substrate; adding at least one labeled probe specific for a portion of the designated genetic sequence to the first and second locations on the substrate; detecting the signal from the at least one labeled probe specific for a portion of the designated genetic sequence at the first and second locations on the substrate, and comparing the signal from the first and second locations on the substrate to detect a designated genetic sequence in the sample of genomic DNA.

In another aspect of this invention a method to detect a designated genetic sequence in a sample of tissue by comparing the sample to a designated control sample of tissue is provided. This method comprising the steps of: treating the sample of tissue and the designated control sample of tissue with a sufficient amount of a lysis buffer to obtain cellular debris including genomic DNA; separating the genomic DNA from the cellular debris for the sample of tissue and the designated control sample of tissue; depositing the genomic DNA from the sample at a first location on a substrate; depositing the genomic DNA from the designated control sample at a second location on the substrate; adding at least one labeled probe specific for a portion of the designated genetic sequence to the first and second locations on the substrate; detecting the signal from the at least one labeled probe, specific for a portion of the designated genetic sequence, at the first and second locations on the substrate, and comparing the signal from the first and second locations on the substrate to detect a designated genetic sequence in the sample of tissue.

According to another aspect of the invention a method to detect a designated genetic sequence in a sample of tissue by comparing the sample with a designated control sample of tissue is provided. This method comprising the steps of: treating the sample of tissue and the designated control sample of tissue with a sufficient amount of a lysis buffer to obtain cellular debris including genomic DNA; separating the genomic DNA from the cellular debris for the sample of tissue and the designated control sample of tissue using magnetic particles; depositing genomic DNA from the sample at a first location on a substrate; depositing genomic DNA from the designated control sample at a second location on the substrate; adding at least one labeled probe specific for a portion of the designated genomic sequence to the first and second locations on the substrate; detecting the signal from the at least one labeled probe, specific for a portion of the designated genetic sequence at the first and second locations on the substrate, and comparing the signal from the first and second locations on the substrate to detect the designated genetic sequence in the sample of tissue.

According to another aspect of the invention a method to detect a designated genetic sequence in a sample of tissue by comparing said sample with a designated control sample of tissue is provided. This method comprising the steps of: treating the sample of tissue and the designated control sample of tissue with a sufficient amount of a lysis buffer to obtain cellular debris including genomic DNA; separating the genomic DNA from the cellular debris for the sample of tissue and the designated control sample of tissue using magnetic particles; adjusting genomic DNA concentration to facilitate detection of the designated genetic sequence; depositing genomic DNA from the sample at a first location on the substrate; depositing genomic DNA from the designated control sample at a second location on the substrate; adding at least one labeled probe specific for a portion of the designated genomic sequence to the first and second locations on said substrate; detecting the signal from the at least one labeled probe, specific for a portion of the designated genetic sequence at the first and second locations on the substrate, and comparing the signal from the first and second locations on the substrate to detect the designated genetic sequence in the sample of tissue.

In another aspect of the invention a method of screening a sample of for a designated genetic sequence by comparing said sample with a designated control sample of tissue the screening method using at least one labeled target binding probe and at least one labeled reference binding probe is provided. This method involves the steps of: treating said sample of tissue and the designated control sample of tissue with a sufficient amount of a lysis buffer to obtain cellular debris including genomic DNA; separating the genomic DNA from the cellular debris for the sample of tissue and the designated control sample of tissue using magnetic particles; depositing genomic DNA from the sample at a first location on a substrate; depositing genomic DNA from the designated control sample at a second location on the substrate; adding at least one labeled probe specific for a portion of the designated genetic sequence to the first and second locations on the substrate; adding at least one labeled reference binding probe to the first and second locations on the substrate; detecting the signal from the at least one labeled probe, specific for a portion of the designated genetic sequence at the first and second locations on the substrate, detecting the signal from at least one labeled reference binding probe at the first and second locations on the substrate; and comparing the signal from the first and second locations on the substrate to screen a sample for the designated genetic sequence.

According to another aspect of the invention method of screening genomic DNA for a designated genetic sequence, wherein a tissue sample, including the genomic DNA, is sent by a remote user to a screening laboratory is provided. The method involves the steps of: facilitating the extraction of genomic DNA from a tissue sample by providing a lysis buffer to a remote user; transmitting the tissue sample from the remote user to the screening laboratory; receiving the lysed tissue sample at the screening laboratory from the remote user; separating the genomic DNA from the lysed tissue sample using magnetic particles; depositing genomic DNA from the sample at a first location on a substrate location; depositing genomic DNA from the designated control sample at a second location on the substrate; adding at least one labeled probe specific for a portion of the designated genetic sequence to the first and second locations on the substrate; adding at least one labeled reference binding probe to the first and second locations on the substrate; detecting the signal from the at least one labeled probe, specific for a portion of the designated genetic sequence at the first and second locations on the substrate, detecting signal from at least one labeled reference binding probe to the first and second locations on the substrate; and comparing the signal from the first and second locations on the substrate to screening a sample for a designated genetic sequence.

According to another aspect of the invention, a method of screening a sample of tissue for a designated genetic sequence, by comparing the sample with a designated control sample of tissue, wherein the tissue samples, including the genomic DNA, are sent by a remote user to a screening laboratory is provided. This method comprising the steps of: facilitating the extraction of genomic DNA from a tissue sample by providing a lysis buffer to a remote user; treating the sample of tissue and the designated control sample of tissue with a sufficient amount of the lysis buffer to obtain cellular debris including genomic DNA; transmitting the tissue samples in the lysis buffer from the remote user to the screening laboratory; receiving the lysed tissue samples at the screening laboratory from the remote user; separating the genomic DNA from the cellular debris for the sample of tissue and the designated control sample of tissue using magnetic particles; depositing genomic DNA from the sample at a first location on a substrate; depositing genomic DNA from the designated control sample at a second location on the substrate; adding at least one labeled probe specific for a portion of the designated genomic sequence to the first and second locations on the substrate; detecting the signal from the at least one labeled probe, specific for a portion of the designated genetic sequence at the first and second locations on the substrate, and comparing the signal from the first and second locations on the substrate to screen the tissue sample for the designated genetic sequence.

According to another aspect of the invention a method of screening genomic DNA, in at least one sample, sent by a remote user to a screening laboratory, for a designated genomic DNA sequence, the remote user providing screening parameters via an electronic communications link to the screening laboratory and a supplier is provided. This method comprising the steps of: transmitting an access request from a remote user to a screening laboratory via an electronic communications link; transmitting an access enabling response from the screening laboratory to the remote user via an electronic communications link, the access enabling response including the screening parameters; selecting screening parameters by the remote user; transmitting the selected screening parameter selections from the remote user to the screening laboratory via an electronic communications link; receiving screening parameter selections from the remote user by the screening laboratory via said communications link; transmitting a request from the screening laboratory via an electronic communications link to a supplier to obtain probes conforming to selected screening parameters; receiving the probes by said laboratory; transmitting the sample from the remote user to the screening laboratory; conducting screening of the sample, according to the selected screening parameters, to obtain data; and transmitting the data to the remote user via an electronic communications link.

According to another aspect of the invention a method of screening genomic DNA, in at least one sample, sent by a remote user to a screening laboratory for a designated genomic DNA sequence, the remote user providing screening parameters via an electronic communications link to the screening laboratory is provided. This method comprising transmitting an access request from a remote user to a screening laboratory via an electronic communications link, transmitting an access enabling response from the screening laboratory to the remote user via an electronic communications link, the access enabling response including the screening parameters; selecting screening parameters by the remote user; transmitting the selected screening parameter selections from the remote user to the screening laboratory via an electronic communications link; receiving screening parameter selections from the remote user by the screening laboratory via the communications link; transmitting a request from the screening laboratory via an electronic communications link to a supplier to obtain probes conforming to selected screening parameters; receiving the probes by the screening laboratory, transmitting the sample from the remote user to the screening laboratory, conducting screening of the sample, according to the selected screening parameters, to obtain data; and transmitting the data to the remote user via an electronic communications link.

According to another aspect of this invention a method of screening genetic DNA, in at least one sample, sent by a remote user to a screening laboratory for a designated genomic DNA sequence, the remote user providing screening parameters via an electronic communications link to the screening laboratory is provided. This method comprising: transmitting an access request from a remote user to a screening laboratory via an electronic communications link; transmitting an access enabling response from the screening laboratory to the remote user via an electronic communications link, the access enabling response including the screening parameters; selecting screening parameters by the remote user; transmitting the selected screening parameter selections from the remote user to the screening laboratory via an electronic communications link; receiving selected screening parameter selections from the remote user by the screening laboratory via the communications link; transmitting a request from the screening laboratory via an electronic communications link to a supplier to obtain probes conforming to selected screening parameters; receiving the probes by the screening laboratory; transmitting a sample of tissue in a lysis buffer from the remote user to the screening laboratory, the lysis buffer formulated to lysis the tissue in the sample during transit time between the remote user and the screening laboratory; conducting screening of the sample, according to the selected screening parameters, to obtain data; and transmitting the data to the remote user via an electronic communications link.

According to another aspect of the invention, an automated apparatus for high volume screening and targeted mutagenesis screening of tissue samples sent by a remote user to a screening laboratory is provided. This method comprising: means for transmitting an access request from a remote user to a screening laboratory via an electronic communications link; means for transmitting an access enabling response from the screening laboratory, to the remote user via an electronic communications link with screening parameters; means for transmitting screening parameter selections from the remote user to the screening laboratory; means for transmitting the sample from the remote user to the screening laboratory; means for isolating genomic DNA from the sample; means for depositing the genomic DNA on a substrate; means for screening genomic DNA; and means for transmitting the data to the remote user.

According to another aspect of this invention a high volume apparatus for screening a tissue sample for modified or mutated genomic DNA according to screening parameter selections made by a remote user is provided. This apparatus includes an automated accessioning station for removing liquid from a first well plate to a second well plate; an isolation station for isolating genomic DNA in the second well plates; an optical standardization station for adjusting DNA concentration in the second well plate; an arraying station for depositing the genomic DNA from the second testing well plate on to a substrate; a hybridization station for hybridizing labeled probes that bind to the portions of the genomic DNA; a detection station for detecting the bound labeled probes; means for making screening parameter selections by a remote user, the remote user communicating with the apparatus through an electronic communications link; and means for communicating screening results to the remote user through an electronic communications link.

According to another aspect of the invention a system of screening genomic DNA in a sample for a designated genomic DNA sequence is provided. The system includes a computer having a processor, memory and web browser wherein the computer is adapted to receive the screening parameter selections from a remote user; and a work station that analyzes samples of genomic DNA for the screening parameter selections wherein the workstation includes a microarray imager.

(9) BRIEF DESCRIPTION OF THE DRAWINGS

A more complete understanding of the invention and its advantages will be apparent from the following Description of the Preferred Embodiment(s) taken in conjunction with the accompanying drawings, wherein:

FIG. 7C is a block diagram of the laboratory process system.

FIG. 7D is a block diagram of the laboratory process system.

FIG. 11 is a graphical representation of the results.

(10) DETAILED DESCRIPTION OF THE PREFERRED EMBODIMENT

Figure 1:
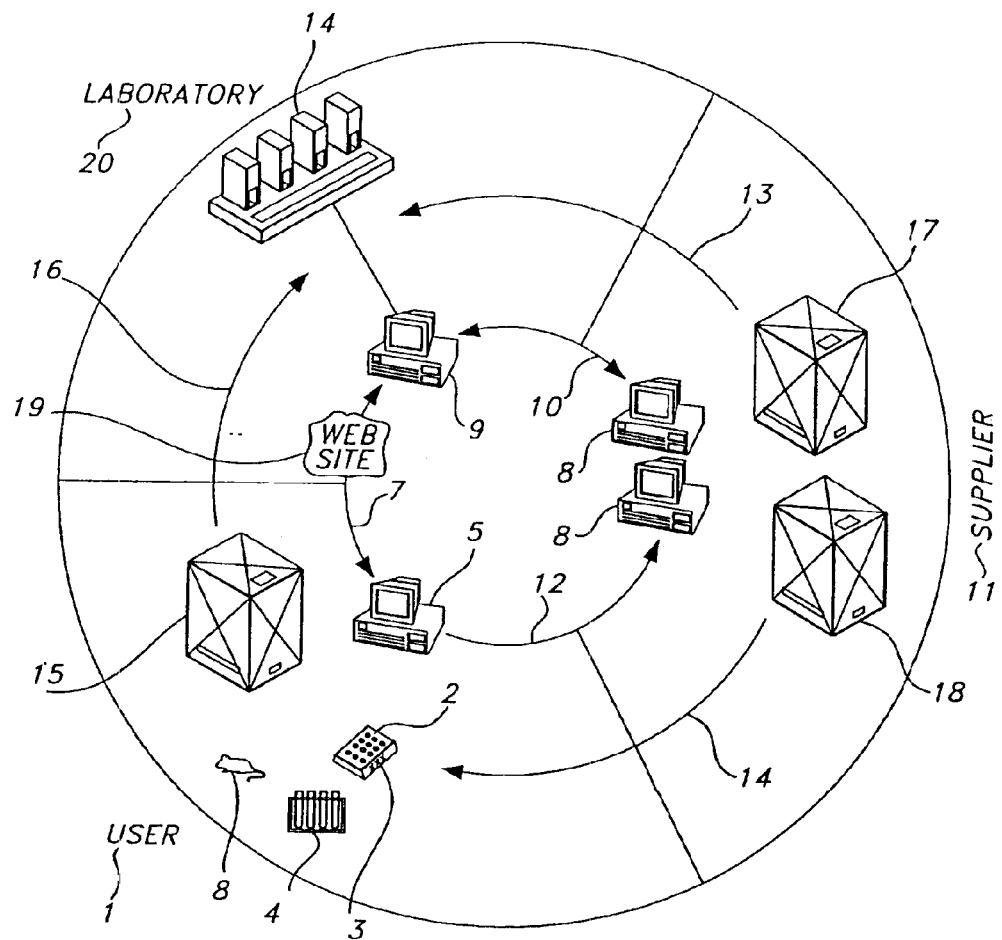
FIG. 1 is an illustrative overview of the remote automated testing procedures of the present invention.

The present invention provides a method and system for high volume transgenic and targeted mutagenesis screening. This invention provides a method for rapid identification of an organism, whose genome possesses specific genetic sequences that exist endogenously or has been modified, mutated or genetically engineered. All patents, patent applications and articles discussed or referred to in this specification are hereby incorporated by reference.

The following terms and acronyms are used throughout the detailed description:

1. Definitions complementary—chemical affinity between nitrogenous bases as a result of hydrogen bonding. Responsible for the base pairing between nucleic acid strands. Klug, W. S. and Cummings, M. R. (1997) Concepts of Genetics, 5$^{th}$ ed., Prentice-Hall, Upper Saddle River, N.J.

copy number—the number of transgenes that have randomly integrated into the genome.

deletion mutation—a mutation caused by the removal of one or more nucleotides from a gene or chromosome.

designated genetic sequence—includes a transgenic insert, a selectable marker, recombinant site or any gene or gene segment.

DNA (deoxyribonucleic acid)—The molecule that encodes genetic information. DNA is a double-stranded molecule held together by weak bonds between base pairs of nucleotides. The four nucleotides in DNA contain the bases: adnine (A), guanine (G) cytosine (C), and thymine (T). In nature, base pairs form only between A and T and between G and C; thus the base sequence of each single strand can be deduced from that of its partner.

electroporation—the exposure of cells to rapid pulses of high-voltage current which renders the plasma membrane of the cells permeable and thus allowing transfection.

embryonic stem cells (ES cells)—a cell of the early embryo that can replicate indefinitely and which can differentiate into other cells; stem cells serve as a continuous source of new cells.

genome—all the genetic material in the chromosomes of a particular organism; its size is generally given as its total number of base pairs.

genomic DNA—all of the genetic information encoded in a cell. Lehninger, A. L., Nelson, D. L. Cox, M. M. (1993) Principles of Biochemistry, 2$^{nd}$ ed., Worth Publishers, New York, N.Y.

genotype—genetic constitution of an individual cell or organism.

germ-line—unmodified genetic material transmitted to progeny via gametes.

gene targeting—the creation of a null or mutant allele by homologous recombination or gene replacement.

heating cassette—housing mechanism for glass substrates while heating imaging cassette—housing mechanism for glass substrate while imaging inducible gene targeting—a method of gene targeting that allows the inducible inactivation (or activation) of a targeted gene by experimental manipulation, such as administration of a drug. Example: Cre recombinase is a site-specific recombinase that catalyzes the excision of DNA flanked by lox recognition sequences. Since the promoter for Cre expression is sensitive to the drug interferon, targeted deletion is inducible.

Internet—a collection of interconnected (public and/or private) networks that are linked together by a set of standard protocols to form a global, distributed network. World Wide Web (hereinafter web) refers to both a distributed collection of interlinked, user viewable hypertext documents (commonly referred to as web pages) that are accessible via the Internet and the user and server software components which provide user access to such documents using standard Internet protocols.

line—A line is a colony bred for a genetic condition.

lipofection—the introduction of transgenes across cell membranes by using liposome vesicles formed by phagocytosis. This method is advantageous in that it is tissue-specific.

microarray imager—is a reader used to detect luminescence from samples bound or affixed to an optically flat substrate.

microarray technology—is a hybridization-based process that allows simultaneous quantitation of many nucleic acid species, has been described (M. Schena, D. Shalon, R. W. Davis, and P. O. Brown, "Quantitative Monitoring Of Gene Expression Patterns With A Complementary DNA Microarray," Science, 270(5235), 467–70, 1995;1 J. DeRisi, L. Penland, P. O. Brown, M. L. Bittner, P. S. Meltzer, M. Ray, Y, Chen, Y. A. Su, and J. M. Trent, "Use Of A Cdna Microarray To Analyze Gene Expressions Patterns In Human Cancer," Nature Genetics, 14(4), 457–60 ("DeRisi"), 1996; M. Schena, D. Shalon, R. Heller, A Chai, P. O. Brown, and R. W. Davis, "Parallel Human Genome Analysis: Microarray-Based Expression Monitoring Of 100 Genes," Proc. Natl. Acad. Sci. USA., 93(20), 10614–9, 1996. This technique combines robotic spotting of small amounts of individual, pure nucleic acids species on a glass surface, hybridization to this array with multiple fluorescently labeled nucleic acids, and detection and quantitation of the resulting fluor tagged hybrids with a scanning confocal microscope. This technology was developed for studying gene expression.

microinjection—a technique for introducing a solution of DNA into a blastocyst or pronucleus of a fertilized egg using a fine microcapillary pipette.

mutation—a heritable change in DNA sequence resulting from mutagens. Various types of mutations including frame-shift mutations, missense mutations, and nonsense mutations.

null mutation—completely eliminates the function of a gene, usually because it has been physically deleted.

recombination—The process by which offspring derive a combination of genes different from that of either parent. In higher organisms, this can occur by crossing over.

recombinant DNA—A combination of DNA molecules of different origin that are joined using recombinant DNA technologies.

retroviral infection—retroviral vectors with recombinant DNA incorporate their genome into the chromosomes of cells it infects.

selectable marker—an approach to facilitate the detection of targeted cells by decreasing the detection of random integrants rather than increasing targeting efficiency. There are two types of selectable genes: designated and negative. A designated selector gene, such as neomycin, confers resistance to drugs normally lethal to the cell. Cells that have incorporated neomycin into their genome by homologous recombination will be resistant to the drug neomycin. Conversely, non-homologous recombination events will retain the negative selector gene. The negative selector gene, such as HSV tk, confers sensitivity to certain drugs (cells expressing HSV tk are sensitive to gancyclovir) resulting in cell death. A selectable marker is a genetic sequence.

site specific recombinase—an enzyme that promotes recombination between specific DNA sequences.

secondary well plate—plate DNA is printed from.

source well plate—The plate that remote user fills with sample and lypholized reagent.

targeted deletion—technique for inactivating a gene by deleting it from the genome. May be accomplished by homologous recombination or inducible gene targeting.

targeted mutagenesis—alteration of the germline by the introduction of a site-directed mutation.

transfection—the uptake, incorporation, and expression of recombinant DNA by eukaryotic cells.

transgene—the foreign gene or DNA.

transgenic—this term describes an organism that has had genes from another organism put into its genome through recombinant DNA techniques. These organisms are usually made by microinjection of DNA in the pronucleus of fertilized eggs, with the DNA integrating at random.

transgenic line—a transgenic mouse or organism strain in which the transgene is stably integrated into the germline and therefore inherited in Mendelian fashion by succeeding generation.

web site—a computer system that serves informational content over a network using the standard protocol of the World Wide Web. A Web Site corresponds to a particular Internet domain name such as TransnetYX.com.

Overview of the Systems Components and Operations

The present invention provides a method and system for transgenic and targeted mutagenesis screening. A system and method operating according to the features described herein can be used to screen about 2000 samples per day, (using only a automated arrayer) or if fully automated about 100,000 samples per day. Additionally, a system and method operating according to the features described herein can provide screening results to a remote user 1 from the screening laboratory 20 within 48 hours of receiving the screening parameter selections for a plurality of samples.

Figure 2:
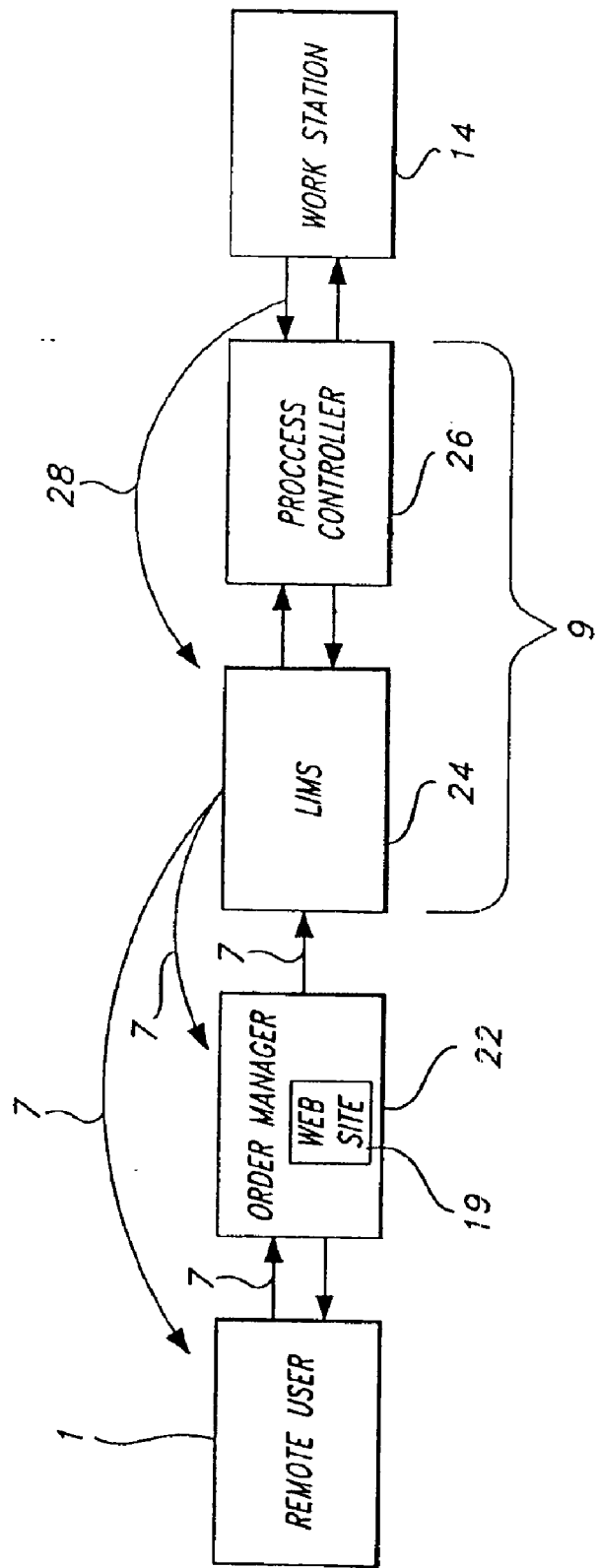
FIG. 2 is a block diagram of one embodiment of the system.
Figure 3:
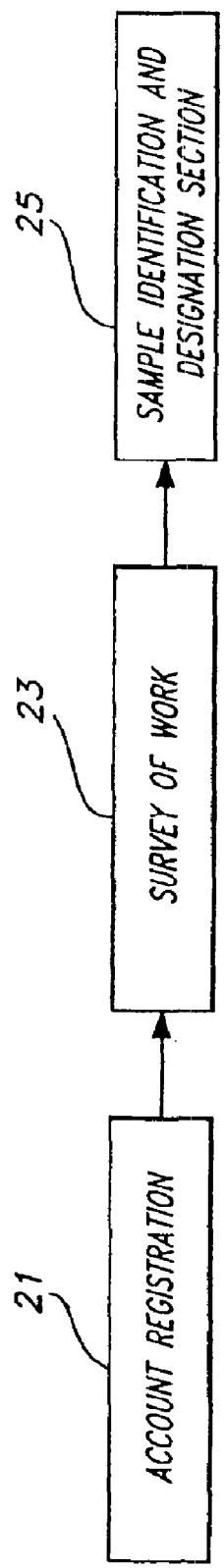
FIG. 3 is a block diagram of the ordering procedure.

FIGS. 1–3 present an overview of certain features of the present invention. The present invention allows a remote user 1 with access to a computer 5 to order transgenic and targeted mutagenesis screening of samples they submit to the transgenic or targeted mutagenesis screening website 19, hereinafter screening laboratory. Using the Internet or other communication link 7, the remote user 1 sends an access request 7 from the remote user's computer 5 to a screening laboratory computer 9 via an electronic communication link 7, such as the Internet. The screening laboratory website 16 will transmit an access enabling response to the remote user 1 via an electronic communication link, such as the Internet. This response includes three distinct sections. The three sections are Account Registration 21, Survey of The Work 23 and Sample Identification and Designation 25.

Now referring to FIG. 2, a remote user 1 can be access screening laboratory's website 19 via a communication link 7. The website 19 can be housed by an order manager 22 such as Dotlogix® (Memphis, Tenn.). An order manager is a software ordering management system. In the preferred embodiment the software is Spaceworks (Manugistics, Inc., (Rockville, Md.). The order manager 22 functions to manage the placement of the order and houses the web site 19. The order received from the remote user 1 as recorded in the website 19, is reported to order manager 22 which is in electronic communication 7 with the screening laboratory computer 9. The screening laboratory computer 9 includes LIMS 24 which is communicatively coupled to a process controller 26.

LIMS 24 is the generic name for laboratory information management system software. The function of LIMS 24 is to be a repository for data, control automation of a laboratory, track samples, chart work flow, and provide electronic data capture. LIMS 24 can also in another embodiment be in direct communication with the remote user 1 via an electronic communications link 7. Any standard laboratory information system software can be used to provide these functions. In the preferred embodiment, the Nautilis® program (Thermal Lab System, Bevereley, Mass.) is used.

The process controller 26 is communicatively coupled to the workstation 14. The process controller provides commands to any portions of the workstation 14 which are amenable to automation. See, e.g. Layne et al., U.S. Pat. No. 5,968,731. For example, the process controller 26 directs the delivery of the probes to the substrate 229 in the hybridization station 96. The workstation 14 is communicatively linked 28 to LIMS 24. In this way, the workstation 14 can provide data to LIMS 24 for the formulation of the outcome report 249, via an electronic communication link 7, such as the Internet, to the order manager 22 or remote user 1. In an alternative embodiment, the remote user 1 can be linked 7 to the screening laboratory 20 by a direct phone line, cable or satellite connection.

Figure 4:
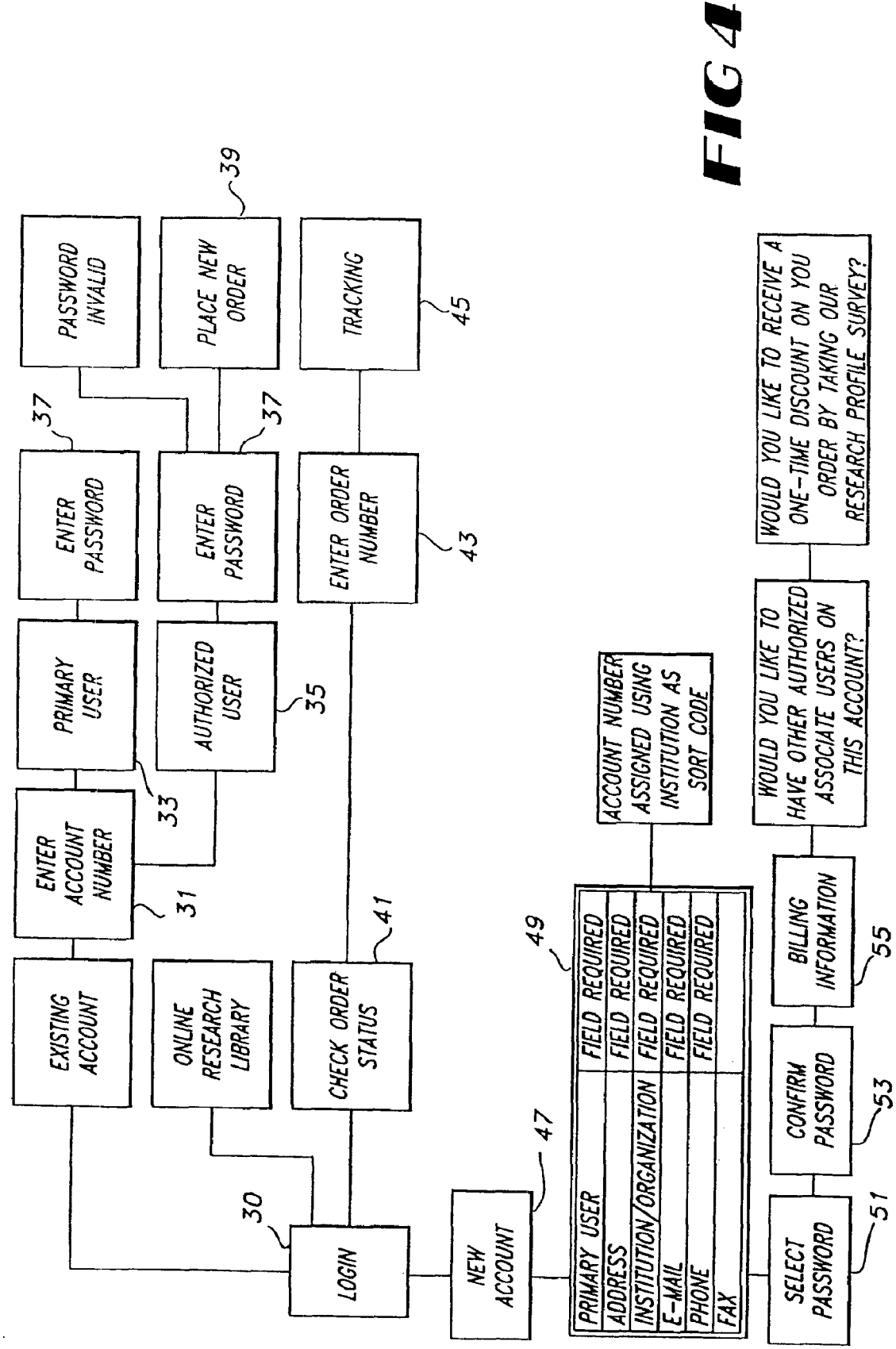
FIG. 4 is a block diagram of account registration.

Now referring to FIG. 4, the user's Account Registration Section 21 requires upon receiving access to the screening laboratory's web site, a remote user 1 accesses an existing account by entering an account number 31. The user will then enter a password. The user is asked whether the user is the primary user 33 or another authorized user 35. If a valid password is entered, the user can place a new order 39. Alternatively, the user can check an order status 41 by providing an order number 43 and can proceed to tracking 45. Alternatively, a new account 47 can by opened by providing institution name, principal investigator, address, phone number, fax number, electronic mail address, billing information, other authorized user names 49. A password is selected 51, confirmed 53 and billing information 55 is provided by the user.

Figure 5:
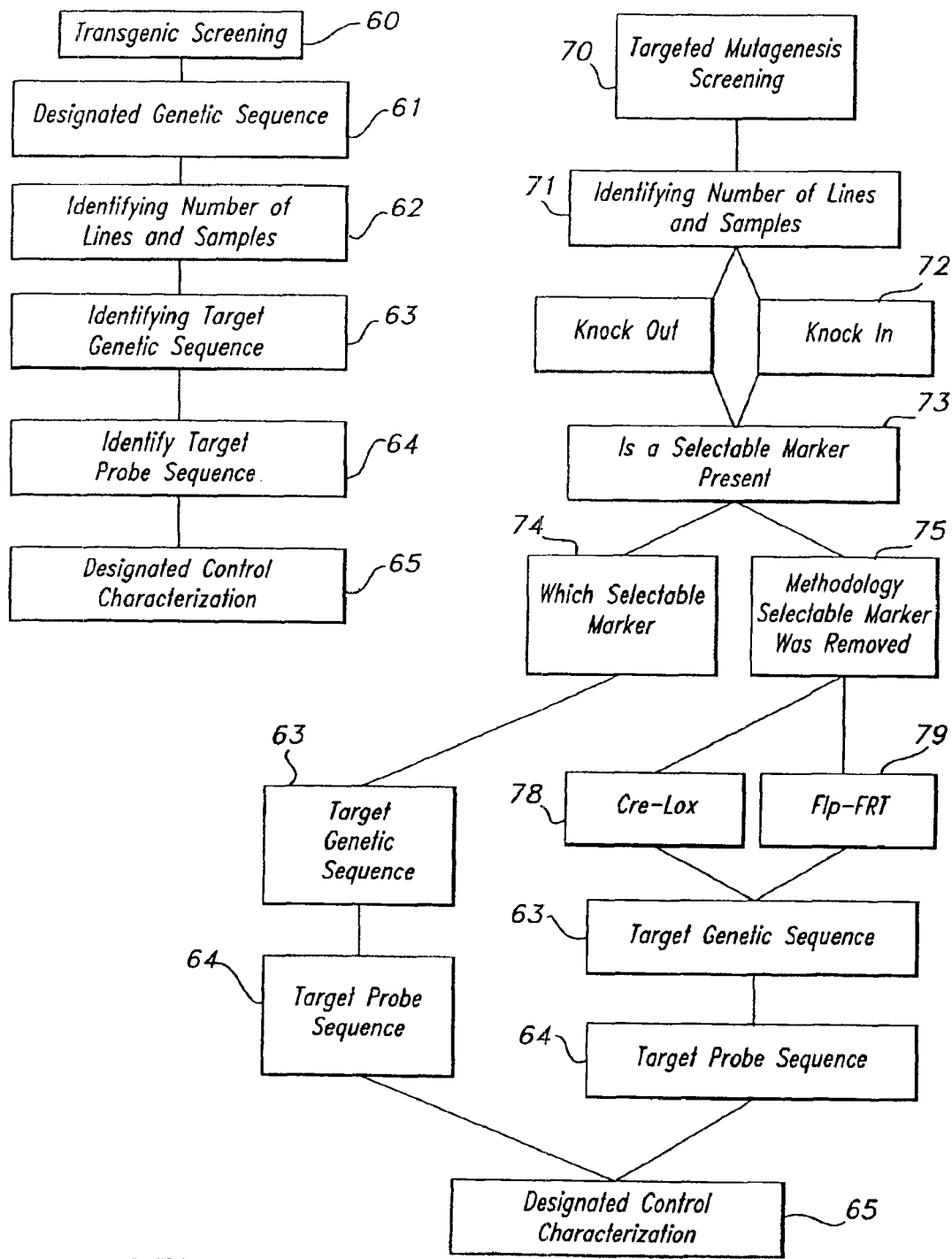
FIG. 5 is a block diagram of survey of work.

The Survey of Work Section 23 has a drop down section that allows a user to make screening parameter selections. Now referring to FIG. 5, these selections include designating if the samples are transgenic 60 or targeted mutations 70. A transgenics organism has genes from another organism put into its genome through recombinant DNA techniques. These animals are usually made by microinjection of DNA into the pronucleus of fertilized eggs, with the DNA integrating at random. The number of copies of the transgene that integrates into the genome is uncontrollable. A transgenic line refers an organism strain in which the transgene is stably integrated into the germ-line and therefore inherited in Mendelian fashion by succeeding generations. A transgene is any foreign DNA sequence or gene.

In the preferred embodiment, mice, i.e. the Genus *Mus*, are screened for transgenic and targeted mutations. Some of the probes designated in the Survey of Work Station 23 are derived from *Mus*. Additionally, a genetic sequence present in all members of a species is used by the screening laboratory 20 as screening reference. For example, in the Genus *Mus*, the major urinary protein MUP can be a reference genetic sequence. Hogan, B., Beddington, R., Constantini, F. and Lacy, E. (1994) Manipulating the Mouse Embryo, $2^{nd}$ ed. Cold Springs Harbor Laboratory Press, Cold Springs Harbor, N.Y.

All species of *Mus* can be screened with this method. Additionally, it is anticipated that other species can be screened according to the present methods. It is well within the ability of one skilled in the relevant art to make screening parameter selections for a different species and for the screening laboratory to select a reference genetic sequence for a different genus species.

If the samples are transgenic 60, the remote user 1 is asked to designate the genetic sequence 61, i.e. the transgenic insert, the number of lines to be tested, the number of samples per line 62, and the target genetic sequence to be targeted per line 63. The target genetic sequence is a portion of the designated genetic sequence and it corresponds to the sequence of the probe. The remote user 1 is asked to identify the probe sequence that is needed to be used for screening (usually 17 to 30 base pairs) per line 64, which is complementary to a portion of the designated genetic sequence. It should be noted that wherever the term "screening" is used, these processes also refer to "detecting". The probe sequence is complementary to the target genetic sequence. The remote user 1 identifies a probe sequence 64 that will hybridize, i.e. bind the target genetic sequence 63, if it is present in the sample. This probe sequence is then communicated to a supplier and the target binding probe made by the probe provider will include this sequence.

The remote user 1 is then asked to identify characterizations 65 about the designated control(s) provided by the remote user 1. The designated control is a genomic DNA sample known to have the designated genetic sequence. The designated control is submitted by the remote user 1 to the screening laboratory 20. Additionally, the remote user 1 provides certain characterizations known about the designated control, include identifying the zygosity, copy number and the mosaic nature of the designated control. The unknown samples copy number can be extrapolated and may accompany the quantitative results relative to the designated control sample.

With respect to targeted mutagenesis screening 70, the remote user 1 is asked to identify the number of lines and samples 71. The remote user 1 is asked if the genetic modification is a knock-out or knock-in 72. If the remote user 1 designated that a selectable marker is present 73, then a choice of marker will be presented to the user 74. The selectable marker sequence is the designated genetic sequence. Common selectable markers include, but are not limited to, the genetic sequence for neomycin resistance, hygromycin resistance and puromycin resistance. Once the remote user 1 identifies which selectable marker is present, the genetic sequence is then presented to the user 1.

Neomysin Sequence

ATGATTGAACAAGATGGATTGCACGCAGGTTCTCCGGCCGCTTGGGTG

GAGAGGCTATTCGGCTATGACTGGGCACAACAGACAATCGGCTGCTCT

GATGCCGCCGTGTTCCGGCTGTCAGCGCAGGGGCGCCCGGTTCTTTTT

GTCAAGACCGACCTGTCCGGTGCCCTGAATGAACTGCAGGACGAGGC (SEQ ID NO:1)

-continued

```
AGCGCGGCTATCGTGGCTGGCCACGACGGGCGTTCCTTGCGCAGCTGT
GCTCGACGTTGTCACTGAAGCGGGAAGGGACTGGCTGCTATTGGGCGA
AGTGCCGGGGCAGGATCTCCTGTCATCTCACCTTGCTCCTGCCGAGAA
AGTATCCATCATGGCTGATGCAATGCGGCGGCTGCATACGCTTGATCC
GGCTACCTGCCCATTCGACCACCAAGCGAAACATCGCATCGAGCGAGC
ACGTACTCGGATGGAAGCCGGTCTTGTCGATCAGGATGATCTGGACGA
AGAGCATCAGGGGCTCGCGCCAGCCGAACTGTTCGCCAGGCTCAAGG
CGCGCATGCCCGACGGCGAGGATCTCGTCGTGACCCATGGCGATGCCT
GCTTGCCGAATATCATGGTGGAAAATGGCCGCTTTTCTGGATTCATCG
ACTGTGGCCGGCTGGGTGTGGCGGACCGCTATCAGGACATAGCGTTGG
CTACCCGTGATATTGCTGAAGAGCTTGGCGGCGAATGGGCTGACCGCT
TCCTCGTGCTTTACGGTATCGCCGCTCCCGATTCGCAGCGCATCGCCTT
CTATCGCCTTCTTGACGAGTTCTTCTGA
```

Hygromycin Sequence

```
ATGAAAAAGCCTGAACTCACCGCGACGTCTGTCGAGAAGTTTCTGAT      (SEQ ID NO:2)
CGAAAAGTTCGACAGCGTCTCCGACCTGATGCAGCTCTCGGAGGGC
GAAGAATCTCGTGCTTTCAGCTTCGATGTAGGAGGGCGTGGATATGT
CCTGCGGGTAAATAGCTGCGCCGATGGTTTCTACAAAGATCGTTATG
TTTATCGGCACTTTGCATCGGCCGCGCTCCCGATTCCGGAAGTGCTT
GACATTGGGGAATTCAGCGAGAGCCTGACCTATTGCATCTCCCGCCG
TGCACAGGGTGTCACGTTGCAAGACCTGCCTGAAACCGAACTGCCCG
CTGTTCTGCAGCCGGTCGCGGAGGCCATGGATGCGATCGCTGCGGCC
GATCTTAGCCAGACGAGCGGGTTCGGCCCATTCGGACCGCAAGGAA
TCGGTCAATACACTACATGGCGTGATTTCATATGCGCGATTGCTGAT
CCCCATGTGTATCACTGGCAAACTGTGATGGACGACACCGTCAGTGC
GTCCGTCGCGCAGGCTCTCGATGAGCTGATGCTTTGGGCCGAGGACT
GCCCCGAAGTCCGGCACCTCGTGCACGCGGATTTCGGCTCCAACAAT
GTCCTGACGGACAATGGCCGCATAACAGCGGTCATTGACTGGAGCG
AGGCGATGTTCGGGGATTCCCAATACGAGGTCGCCAACATCTTCTTC
TGGAGGCCGTGGTTGGCTTGTATGGAGCAGCAGACGCGCTACTTCGA
GCGGAGGCATCCGGAGCTTGCAGGATCGCCGCGGCTCCGGGCGTAT
ATGCTCCGCATTGGTCTTGACCAACTCTATCAGAGCTTGGTTGACGG
CAATTTCGATGATGCAGCTTGGGCGCAGGGTCGATGCGACGCAATCG
TCCGATCCGGAGCCGGGACTGTCGGGCGTACACAAATCGCCCGCAG
AAGCGCGGCCGTCTGGACCGATGGCTGTGTAGAAGTACTCGCCGATA
GTGGAAACCGACGCCCCAGCACTCGTCCGAGGGCAAAGGAATAG
```

Puromycin Sequence

```
ATGACCGAGTACAAGCCCACGGTGCGCCTCGCCACCCGCGACGACGTCCCCCGGGC      (SEQ ID NO:3)
CGTACGCACCCTCGCCGCCGCGTTCGCCGACTACCCCGCCACGCGCCACACCGTCGA
CCCGGACCGCCACATCGAGCGGGTCACCGAGCTGCAAGAACTCTTCCTCACGCGCG
```

-continued

```
TCGGGCTCGACATCGGCAAGGTGTGGGTCGCGGACGACGGCGCCGCGGTGGCGGTC

TGGACCACGCCGGAGAGCGTCGAAGCGGGGGGCGGTGTTCGCCGAGATCGGCCCGCG

CATGGCCGAGTTGAGCGGTTCCCGGCTGGCCGCGCAGCAACAGATGGAAGGCCTCC

TGGCGCCGCACCGGCCCAAGGAGCCCGCGTGGTTCCTGGCCACCGTCGGCGTCTCGC

CCGACCACCAGGGCAAGGGTCTGGGCAGCGCCGTCGTGCTCCCCGGAGTGGAGGCG

GCCGAGCGCGCCGGGGTGCCCGCCTTCCTGGAGACCTCCGCGCCCCGCAACCTCCCC

TTCTACGAGCGGCTCGGCTTCACCGTCACCGCCGACGTCGAGTGCCCGAAGGACCGC

GCGACCTGGTGCATGACCCGCAAGCCCGGTGCCTGA
```

The remote user 1 is asked to review the sequence base-by-base and confirm that the sequence presented is indeed present in their sample 74. A portion of the selectable marker is designated as the target genetic sequence 63. The probe sequence is designated 64. The probe sequence 64 binds to the target genetic sequence 63.

If the remote user 1 indicates that the selectable marker has been removed or that the sample has undergone site-directed recombinant mutations 75. The remote user 1 is directed to indicate which recombinant technology was employed to mutate their samples. The remote user 1 is presented with common recombinant technologies, which may include, but are not limited to Cre-lox 78 and yeast FLP/FRT 79. After selecting one of the techniques a sequence such as
ATAACTTCGTATA ATGTATGC TATACGAAGTTAT (SEQ ID NO:4) and
GAAGTTCCTATAC TTTCTAGA GAATAGGAACTTC C GAATAGGAACTTC CTTCAAGGATATG AAAGATCT CTTATCCTTGAAG G CTTATCCTTGAAG (SEQ ID NO:5)
is presented to the remote user 1, which correlates to Lox-p site 78 and FRT site 79, respectively. The remote user 1 is asked to review the sequence base-by-base and confirm that the sequence presented is indeed present in their sample. The recombinant sites are the designated genetic sequences for selectable marker removal. The remote user 1 designates a target genetic sequence which corresponds to a portion of the recombinant sequence 78 or 79. The remote user 1 identifies a probe sequence 77 that will hybridize, i.e. bind the target genetic sequence 63 if it is present in the sample. This probe sequence 77 is then communicated to a supplier and made according to the designation.

The remote user 1 is then asked to identify characterizations about the designated control(s) provided by the remote user 1. The designated control is a genomic DNA sample known to have the designated genetic sequence. The designated control is submitted by the remote user 1 to the screening laboratory 20. Additionally, the remote user 1 provides certain characterizations known about the designated control, include identifying the zygosity, copy number and the mosaic nature of the designated control. The unknown samples copy number can be extrapolated and may accompany the quantitative results relative to the designated control sample.

In the preferred embodiment, remote user 1 is asked to identify their name, unique pre-registered account number, password and submit their order to the company. The insert for a transgenic sample or genetic sequence of the selectable marker for targeted mutagenesis screening can be collectively referred to as the designated genetic sequence. The target is any subset of the designated genetic sequence.

Figure 6:
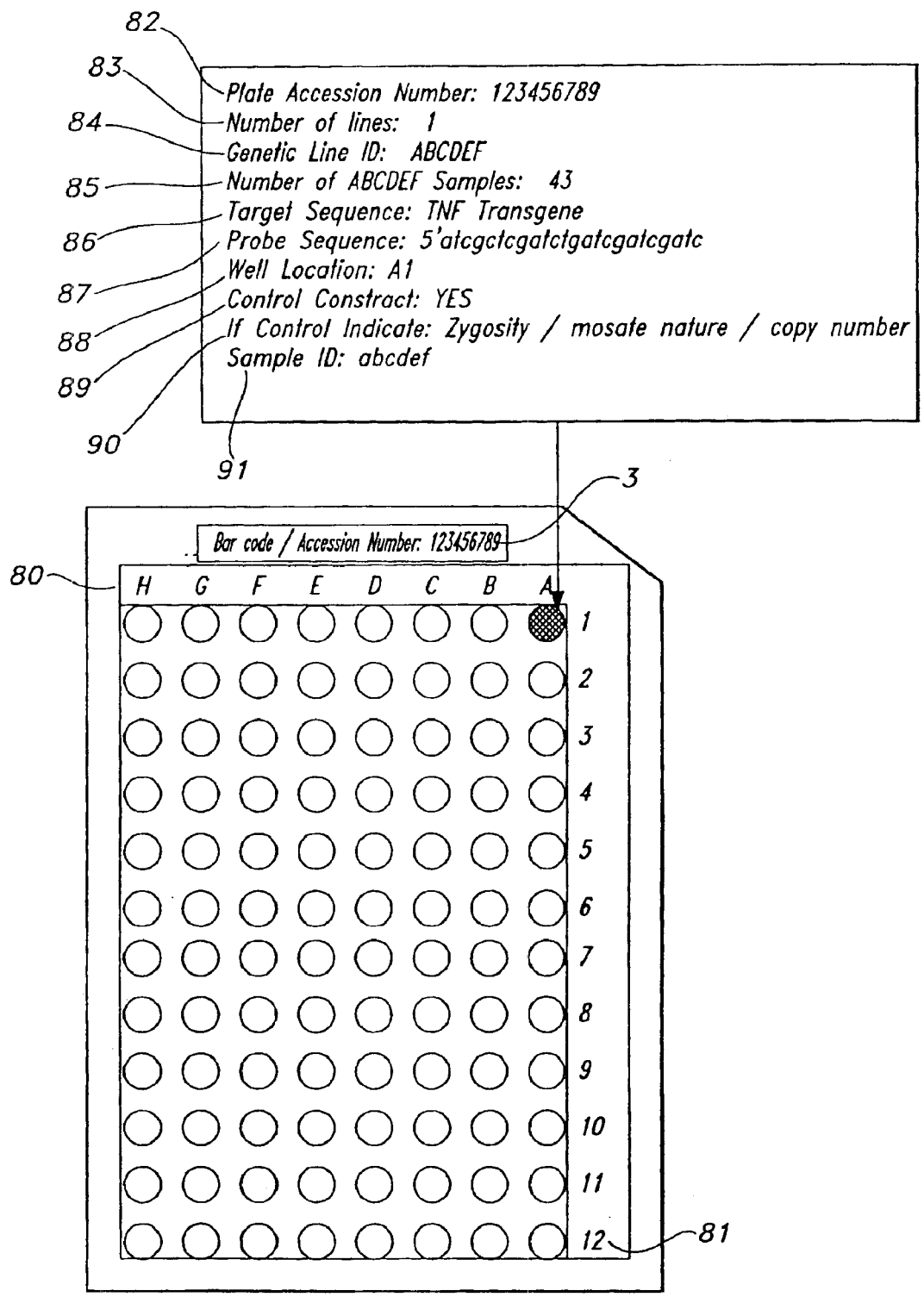
FIG. 6 is an illustration of orientation for sample identification and designation.

Now referring to FIG. 6, once the remote user 1 submits the Survey of Work Section the remote user 1 will be presented with the Sample Identification and Designation Section 25. The Sample Identification and Designation section 25 includes 96 well plate locations. The remote user 1 designates which sample was placed into each well. If the remote user 1 has more than 96 samples, subsequent 96 source well plates and designations are available. With respect to FIG. 6, a 96 well plate having a barcode accession number 3 will be shown oriented in the longitudinal direction having X axis labeled H to A and Y axis labeled 1 to 12 80. The X and Y axis designate a well position such as A1 81.

Now referring to FIG. 6, the remote user 1 is asked to provide: plate accession number 82, number of lines 83, genetic line identification 84, number of samples 85, target sequence 86, probe sequence 87 and well location 88. The remote user 1 is then asked if the material deposited in well A1 is a control. If the material is a control 89, than the remote user designates the zygosity, mosaic nature and copy number of the material 90. If all of these parameters are not known, then the remote user enters as much information as is known. The remote user 1 is then asked for any internal sample identification number 91.

Now referring to FIGS. 1 and 2, the remote user 1 transmits his or her order including the completed screening parameter selection to the screening laboratory 20 via a form of electronic communication 7 such as the Internet or a direct line. The remote user 1 can transmit the selected screening parameter selections to the screening laboratory via an electronic communications 7 link. This link 7 can be direct or indirect. In the indirect route the screening parameters are transmitted to web site 19, wherein order manager 22 provides LIMS 24 with the screening parameter selections. In the preferred embodiment, the order generates two electronic messages, which will be sent to different locations. The first message is cross-referenced in LIMS 24 with a list of stocked probes and if the probe designated by the user, is not stocked an order message is sent to a supplier 16, such as a contracted probe provider. This request can be transmitted from remote user 1 to screening laboratory 20 via any form of electronic communication, and then via a form of electronic communication 10 to suppliers' computer 8, or in the alternative, the order message can go from user 1 via any form of electronic communication 12 to suppliers' computer 8.

This supplier 11 creates the probe that the remote user 1 has designated in their order for the screening the genomic DNA for the designated genomic sequence. The made to order probe can be referred to as the target binding probe. This supplier 11 will then barcode and overnight ship 13 the target binding probe to the screening laboratory 20. Once the target binding probes for each order for that days screening, is received by screening laboratory 20, the barcodes on the target binding probes are scanned into LIMS 24. The LIMS 24 records the date and time the target binding probes were received along with the quality control data provided from the probe provider.

In the preferred embodiment, the target binding probes are placed on in workstation 14 and LIMS 24 will record the barcode of the probe and record its specific location on the deck of the workstation 14, as will be discussed in more detail with respect to the Hybridization Station 96. Additionally, the screening laboratory 20 and the LIMS 24 system correlates which target binding probes will be used on which samples, as will be discussed in more detail in the Hybridization Sections 96.

The second message, in the preferred embodiment, that is generated from the order placement of the remote user 1 will be to ensure the users have the proper supplies to package and ship their samples. This message will define the number of well plate(s), shipping labels and amount of reagents needed for the user. This request will be cross-referenced with an inventory list located in LIMS 24 at the remote user's location. This request can be sent from the remote user 1 to laboratory 20 via any form of electronic communication 7, and then via a form of electronic communication 10 to suppliers 11 or suppliers' computer 8, or in the alternative, the request can go from the remote user 1 via any form of electronic communication 12 to suppliers 11. If the appropriate amount of supplies are located within the user's facility a message will be sent to the user defining the location where they can procure the shipping material needed. However, upon cross-referencing known inventories if a sufficient number of supplies cannot be confirmed at the user's location these items will then be packaged 18 and shipped to the user 14. The remote user 1 will receive a message to inform them that materials are being shipped to them with an expected time of arrival.

Once the remote user 1 procures or receives these supplies, they place the appropriate samples into the source well plates 2. The samples can be obtained from prokaryotic or eukaryotic organisms. The samples may be a tissue sample from a mouse 8, but can also come from other animals and plants. In the preferred embodiment, mouse tails or ears are snipped to provide a tissue sample. A source well plate 2 is a 96 well plate or the like that receives the tissue sample and a sufficient amount of lysis buffer to cover the tissue sample during transit to the screening laboratory 20. A source well plate 2 has an accession number 3 affixed to the side of the plate. The accession number is used by LIMS 24 to track the source of well plate 2. The remote user 1 places the appropriate samples into the well locations in the source well plate 2 that they had previously designated while placing their order FIG. 6. Once the samples are in the proper wells in the source well plate 2 then the remote user 1 dispenses a predetermined amount of reconstituted lyophilized buffer 4 to cover the sample into each well using a pipette. The buffer is formulated to lysis the tissue to obtain cellular debris including genomic DNA. More specifically, the buffer is formulated to lysis the sample while in transit between remote user 1 and the screening laboratory 14. The transit time is approximately 24 hours as all samples are shipped via an express delivery service, such as Federal Express® (Memphis, Tenn.). More specifically, for example, the buffer can be made of (4M Urea, 0.1 M Tris-HCl (pH ~7.5), 1-mM NaCl, 10 mM EDTA, 1% SDS, 5 mM DDT and 415 mg of proteinase K and RNase). The remote user 1 will add lysis buffer 4 to each well of the source well plate 2. The buffer 4 should completely cover the samples. Once the samples and lysis buffer are in the source well plate 2 then a seal will be placed on the top of the source well plate 2 preventing samples from leaking. A plastic lid will then be placed on the seal for transportation. The remote user 1 will then place the source well plate 2 into an overnight delivery service package 15. The remote user 1 will then seal the package and ship 16 to screening laboratory 20, and apply a barcode shipping label.

Figure 7A:
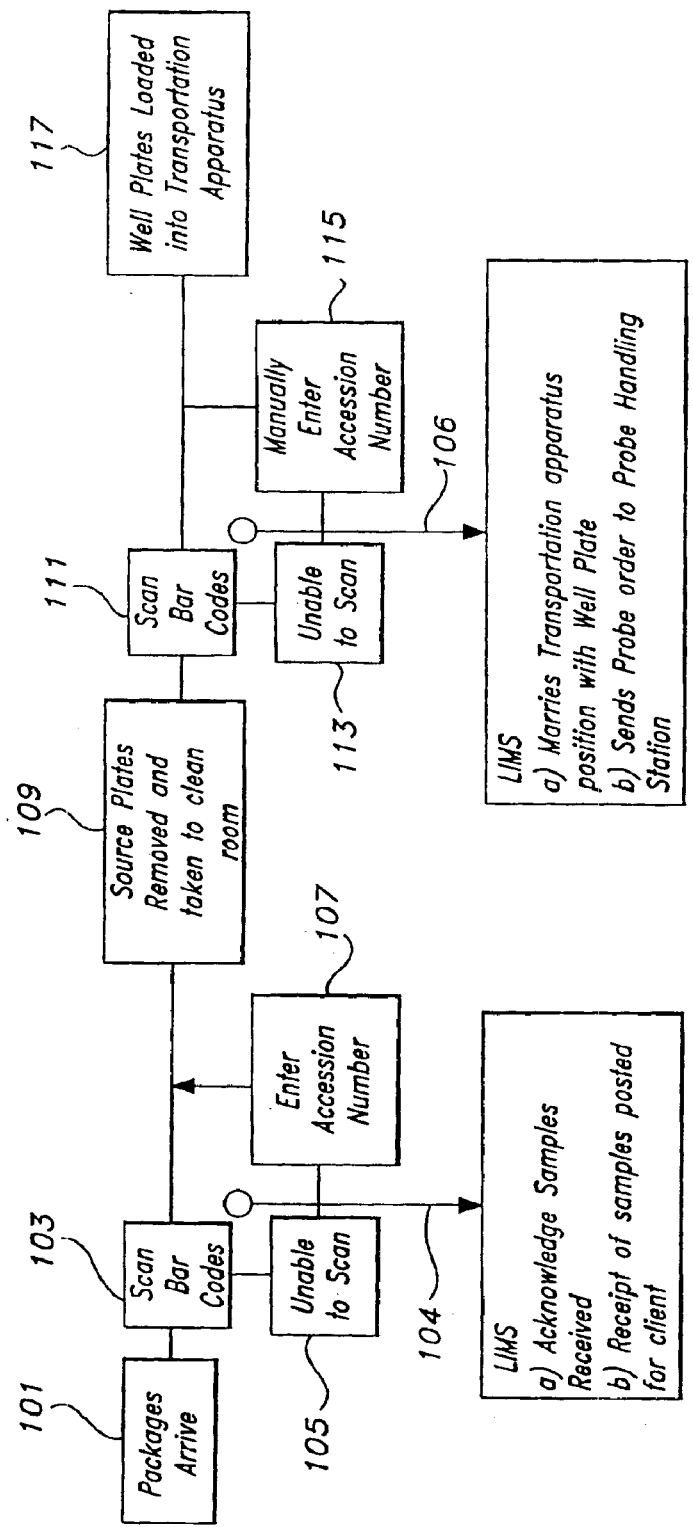
FIG. 7A is a block diagram of the laboratory process system.
Figure 7B:
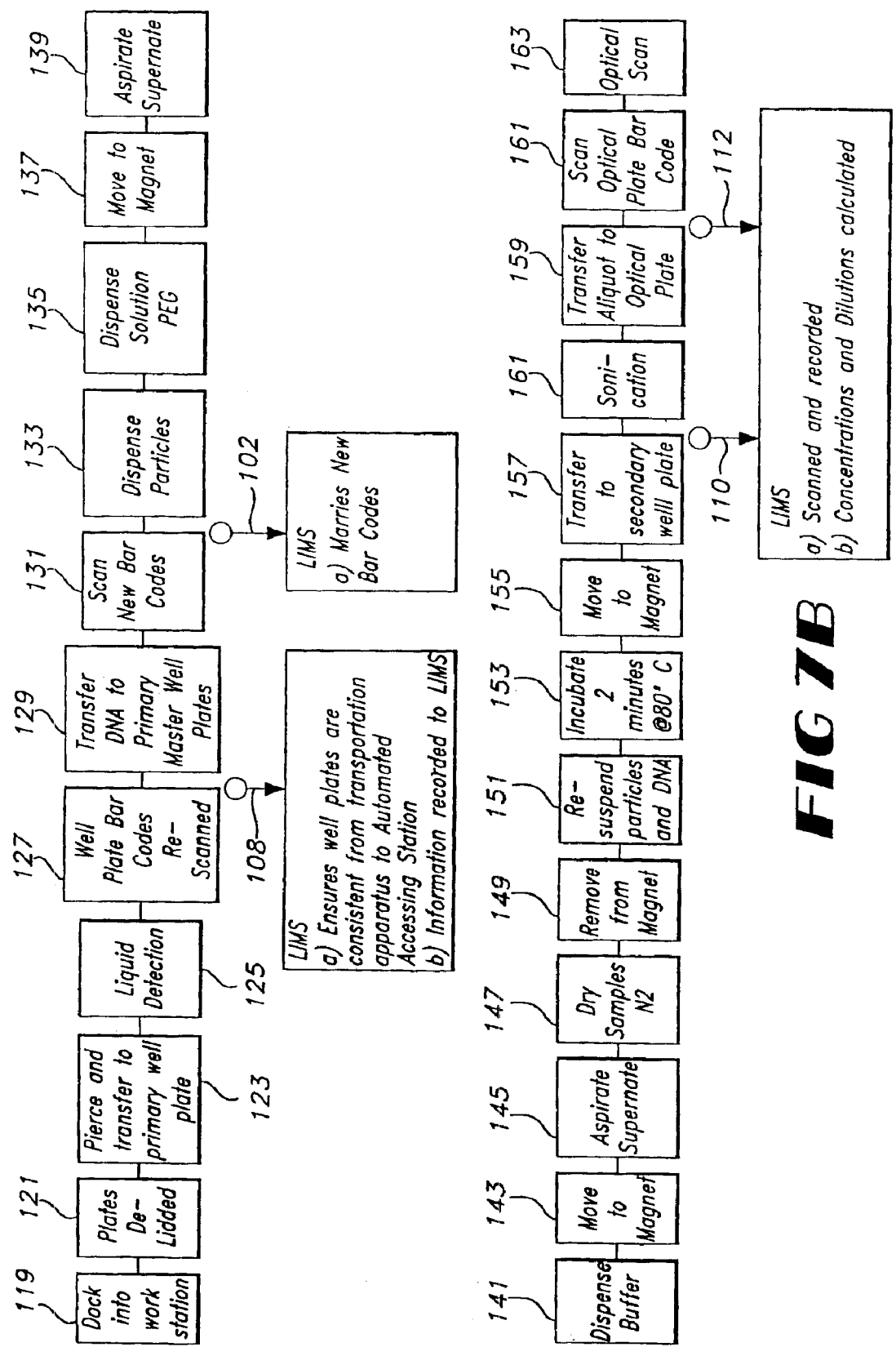
FIG. 7B is a block diagram of the laboratory process system.

Now referring to FIGS. 7A–D, the preferred embodiment of the present invention is shown. In FIG. 7A, the source well plates 2 arrive 101 at the screening laboratory 20. The tracking number of the shipping label is read with a barcode reader 103. If the shipping label is unreadable 105, the tracking numbers are manually entered 107. The scanning of the tracking number is received 104 in LIMS 24 and a received message is posted to the user's account as shown in tracking field. The source well plates 2 are removed from the package and taken to a clean room 109. The source well plates 2 contain the raw biological matter and lysis buffer. The source well plates 2 individual barcodes are scanned by the barcode reader 111 and recorded 106 in LIMS 24 as accession numbers. LIMS 24 can send 106 probe order to supplier 11 through the order manager 22. If the source well plates 2 individual barcodes are unable to be scanned 113, the accession number are entered manually 115. If the tracking number, accession number user order and worklist properly correlate, LIMS 24 will activate (not shown) an active record number for the plates.

The source well plates 2 are loaded 116 into a transportation apparatus in a clean room. A transportation apparatus is any device that holds well plates and that can dock with the workstation. The transportation apparatus, in the preferred embodiment, includes several rigid trays stacked vertically in a housing unit that is mobile. This transportation apparatus can be moved between different automated stations, docked and the rigid trays can be removed in an automated fashion and processed on the deck of a workstation. Each rigid tray consists of nine locations for well plates. Each of these nine locations per tray has a unique barcode designating its specific location inside the transportation module.

The source well plate 2 accession number 3 is scanned with a barcode reader and the barcoded well plate location in the transportation apparatus is scanned. The barcodes of the source plates 2 are married 106 in LIMS 24 with the unique barcode locations in the transportation apparatus for tracking purposes. The source well plate 2 is physically placed 117 into the transportation apparatus. LIMS 24 records and associates 106 the well plate to this location. Once the transportation apparatus is loaded with the source well plates 2, the transportation apparatus is docked 119 into the work station 14.

LIMS 24 will generate a worksheet for laboratory personnel (not shown). The worksheets outline the number of assay plates required and the various probes that will be needed. The LIMS 24 worklist will generate a single file. The file format may include but not limited to ASCII, XML or HTML. The file will be written into a specified directory on the network drive. The name of the file will be unique and will correlate to a run number. The extension will be unique for worklist files.

Figure 8:
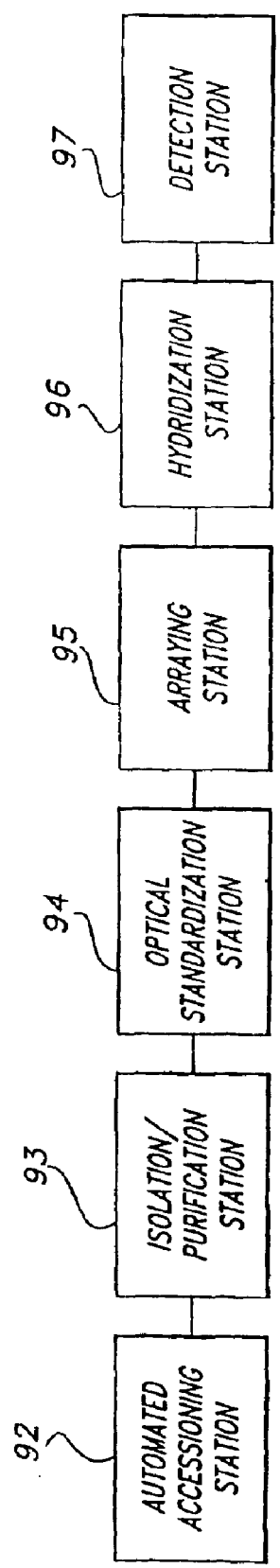
FIG. 8 is a block diagram of standard laboratory stations.

Now referring to FIG. 8, a block diagram depicting one embodiment of the work station. Standard laboratory stations are logical groupings of laboratory operations. These groupings, however, do not necessarily refer to different physical stations. These groupings included: Automated Accessioning Station 92, Isolation/Purification Station 93, Optical Standardization Station 94, Arraying Station 95, Hybridization Station 96 and Detection Station 97.

The following description provides the preferred embodiment, although one skilled in the art could elect to conduct these methods with varying degrees of automation as required.

Automated Accessioning Station 92

An automated accessioning station 92 provides a device to remove liquid from the source well plate 2 to the primary master well plate. The primary master well plate is the plate in which the DNA is isolated. Any commercially available automated accessioning device can perform this function such as Genesis® Tecan (Raleigh-Durham, N.C.) or Multimeck® Beckman (Indianapolis, Ind.). These devices are referred to as liquid handlers. The liquid handler delids the rigid plastic cover of the source plate 121. In the preferred embodiment, liquid detection is performed by the liquid handler by piercing the barrier sealing mechanism 123. The liquid handler performs liquid detection to verify the existence of the original sample 125. The source well plates 2 barcodes are re-scanned 127. This measurement will be recorded and posted 108 into the LIMS 24 database and reflected in the outcome report 249. Additionally, LIMS 24 ensures 108 that well plates are consistent from transportation apparatus to the Automated Accession Station 92. Error codes will be generated if insufficient amount of raw testing material is available. The liquid handler utilizes stainless steel, or the like, pipette tips that are washed between each sample transfer.

The DNA is transferred 129 to clean well plates, referred to a primary master well plate. The barcodes of the primary master well plates are scanned 131 and LIMS 24 marries 102 to the new barcodes for the primary well plates The automated process accessioning continues until all of the days pending samples are accessioned into the primary master well plates.

Isolation/Purification Station 93

The tray of primary matter well plates is moved by the transportation apparatus to the Isolation/Purification Station 93. In this station, the genomic DNA will be isolated and purified using a separation method such as magnetic or paramagnetic particles. The term "magnetic" in the present specification means both magnetic and paramagnetic. The magnetic particles can range from 0.1 micron mean diameter to 100 microns in mean diameter. The magnetic particles can be functionalized as shown by Hawkins, U.S. Pat. No. 5,705,628 at col. 3 (hereinafter '628 patent hereby incorporated by reference). In the preferred embodiment, the magnetic particles are 1 micron carboxylated iron core particles, but other magnetic particles with different functional groups of different size can be used.

For example, in the Isolation/Purification Station 93, each well of the primary master well plate is filled with magnetic particles 133. The particles are dispensed into the well via a syringe pump. A second syringe pump dispenses a binding buffer into the wells containing the raw biological material and active particles 133. The dispensing itself may be sufficient to facilitate mixing of the samples. A secondary mixing mechanism, such as a tip can aspirated and redispense the liquid. A binding buffer, such as, 20% polethylene glycol (PEG) 8000, 0.02% sodium azide and 2.5M sodium chloride is used to non-specifically bind the genomic DNA to the surface chemistry of the magnetic particles. The PEG allows for hydrogen binding of water, which causes concentration of the DNA. Additional binding parameters are disclosed in Hawkins' 628 patent. The particles, binding buffer and raw biological material are allowed to incubate at room temperature for ten minutes. After incubation, a magnet contacts the bottom of the primary master well plates for several minutes, i.e. two to six minutes 137. The magnetic particles with attached genomic DNA are magnetically attracted to the bottom of the master well plates forming a pellet of particles. The supernatant is removed 139. A wash buffer, for example 70% ethanol and 30% de-ionized water, is used to resuspend the particles 141. The magnetic particles with the attached genomic DNA is separated from the supernatant using a magnet 143. The supernatant is aspirated 145. The particle washing step is repeated two to four times.

The primary master well plates with pelletized particles are air dried 147. In an alternative method, the pelletized particles can be dried with compressed nitrogen. Once the particles are completely dry, the magnet is removed 149. The particles with attached genomic DNA are resuspended in a suspension buffer 151. A suspension buffer formulated to elute the bound DNA from the particles. An example of one such suspension buffer is 0.01 M Tris (pH 7.4), 0.02% Sodium Azide or Sodium Saline citrate (SSC), dimethyl sulfoxide (DMSO), sucrose (20%) or foramide (100%). In the preferred embodiment, the primary master plates are heated 153 to 80° C. for two minutes to disassociate the DNA from the particles.

After heating and resuspending the DNA in solution, the magnetic particles are separated from the purified DNA using a magnet 155. The supernatant is removed 157 from the particles and pipetted into a secondary well plate 2. The barcode of the secondary well plate is read. LIMS 24 will correlate the barcodes of the primary and secondary well plates 114. A small amount (1–10 µl) of DNA supernatant is pipetted 159 into a clean barcoded optical 1536 well plate.

If a fully automated system is desired, the magnetic separator can be automated and rise from the bottom of the workstation and make contact with bottoms of all primary well plates simultaneously.

In one embodiment, the genomic DNA can be sonicated before or after separation with the magnetic particles 161. In the preferred embodiment, the genomic DNA is sonicated after separation from the cellular debris. Sonication can be done by any conventional means such as a fixed horn instrument. In the preferred embodiment, the genomic DNA is sonicated for 5 minutes to produce DNA fragments. Although there is a wide range of fragments from about 100 base pairs to up to 1 kilobase, the average size of the fragment is around about 500 base pairs (about meaning 50 base pairs).

Optical Standardization and Well Plate Station 94

Optical Standardization involves DNA quantification. An optical plate, such as a 1536 well plate with a clear bottom from which an absorbent reading can be measured, is provided. In the preferred embodiment, a 1536 ULTRAMARK (Bio-Rad, Hercules, Calif.) is used. The barcode of the optical plate is scanned 161. Small aliquots of DNA supernatant from the secondary master well plates are tracked 110 via LIMS 24 to specific well locations within the DNA concentration optical well plate. The optical well plate is subjected to a DNA concentration analysis 163. This analyses involves an optical density scan (260/280 ratio) or a fluorometry as known by one skilled in the art. The DNA concentration values are quantified and recorded 112 in LIMS 24.

The concentration of genomic DNA in the secondary well is adjusted to preferably be with in the range of about 12.5 to 500 ng/µl of fluid in the secondary master well plate and more preferable to be within the range from 17 ng to 250 ng/µl of fluid in the secondary master well plate.

The optical standardization station 94 performs adjustments based on known sample volumes in secondary master well plates with the known DNA concentration to calculate the volume to hydrate or the time to desiccate each sample. The secondary well plate samples may be hydrated with de-ionized water by the automated liquid handler system to decrease the DNA concentration 165. Conversely, samples may be desiccated for a calculated time frame with compressed gas to concentrate the DNA samples 167. If the DNA concentration is zero or the quantification value falls below the parameters for optimization the LIMS 24 will generate an insufficient quantity report to be noted on the outcome report (not shown). The optimized sample 169, in the secondary master well plates are re-scanned for concentration verification 171.

Arraying Station 95

Figure 9:
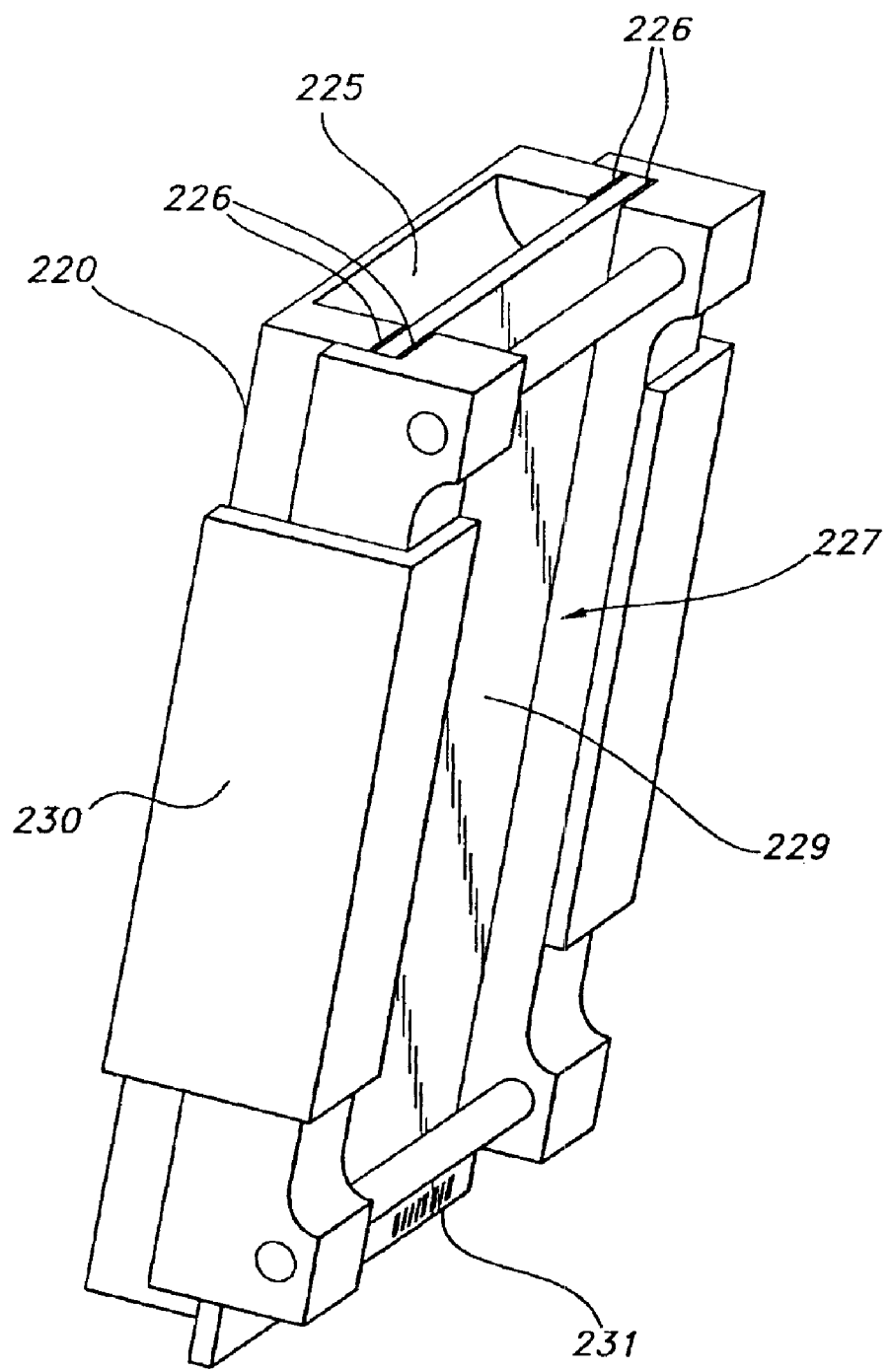
FIG. 9 is an illustration of a heating cassette.

In the arraying station 95, a sample of genomic DNA from the secondary well plate is deposited on a substrate 229. A substrate is shown in FIG. 9. A substrate 229 is optically flat so that it can be scanned with a laser and it includes a sufficient number of functional groups to bind the genomic DNA to be screened. The substrates 229 may be glass, plastic, membranes, or a combination of the elements. Typically the substrates 229 have some surface chemistry attached. These surface chemistries include by not limited to amine groups, aldehydes groups or polylysine. The reactive groups covalently or non-covalently attach the nucleic acid (DNA, cDNA, EST, Amplicon, etc.) to the surface of the substrate 229. In the preferred embodiment, aldehyde function groups ($5.0 \times 10^{12}$), reactive groups per $cm^2$ are affixed to optically flat glass slide. The slide (SMA-1000) is purchased from TeleChem (Sunnyvale, Calif.).

In the array station 95, the genomic DNA is deposited 175 on the surface of the substrate 229 with a solid pin tool using the automatic arrayer. An arrayer is a machine that dips titanium tips, or the like, into wells and prints on substrates. An automatic arrayer includes software that tracks the location of a specific samples with its location on the substrate. The arrayer is communicatively coupled to LIMS 24 and information on each sample is transmitted 114 to LIMS. Typically, automatic arrayers include, but are not limited, to solid pin, split pin/quill, tweezer, TeleChem's Micro Spotting Pin (Sunnyvale, Calif.), pin and ring, piezoelectric technology and syringe-solenoid technologies. An automatic arrayer can be used in this method according to the manufactures operating instructions without modification.

With the aldehyde coated slides, the genomic DNA spots do not need to be processed further for attachment to the substrate. However, using other functional groups, the genomic samples is attached on the substrates 229 by ultra-violetly cross-linked to the surface and/or thermally heating to attach the samples. For example, the genomic DNA is ultra-violetly attached to the substrate at 1200 $\mu$/j for thirty seconds. Similarly, heating at 80° C. for 2–4 hours will also accomplish the attachment. The spots on the substrate 229 are from between 1–100 microns in size. Between approximately 1–130,000 genomic DNA spots, corresponding to discrete trackable samples are located on an individual substrate 229.

Now referring to FIG. 7C, for example, the substrates barcode 231 is scanned 173. LIMS 24 associates 118 well plate and substrate barcodes 231. Additionally, LIMS 24 associates 114 the substrate barcodes 231 with a specific sample with a location on the substrate. Genomic DNA from the samples to be tested and genomic DNA from the designated control provided by the remote user 1 are deposited on the substrate in assigned locations, for example if referring only to the testing of one tissue sample, the first and second locations on the substrate. Prior to depositing the genomic DNA on the substrate, the genomic DNA samples are mixed with a sufficient amount of spotting buffer to facilitate deposition on the substrate 229.

In the preferred embodiment, the spotting buffer is 3×SSC, but other equivalent buffers may be used including DSMO, 1×SSC or commercial spotting buffers. The genomic DNA is deposited 175 on to the substrate 229. The sample of genomic DNA is deposited three times on the substrate 229 for quality control purposes. LIMS 24 records 114 the precise location of the deposited genomic DNA samples on the substrate 229 from information received from the automated microarray device. In an alternative embodiment, at least one probe specific for a reference genetic sequence is also added to each spot. The probe is specific for the reference genetic sequence.

In another alternative embodiment, a small amount of morphology sequence nucleic acid is added 177 to each well of the secondary well plate. The morphology sequence may be any nucleic acid sequence derived from any source, such as prokaryotes or eukaryotes that does not naturally occur in the genome of biological material being tested. Lambda DNA spiked into the sample could be used as a morphology control. Examples of morphology sequence may include but not limited to exogenous genes, partial genes, tandem repeats, arbitrary sequences or synthetic oligonucleotides. The morphology sequence is pipetted into the genomic DNA of the secondary well plate and mixed by gently pipetting up and down. The morphology control is used to determine if sample was successfully transferred to the substrate 229.

Now referring to FIG. 7D, in the preferred embodiment, after the depositing onto the substrate 229 is completed the secondary well plates are off loaded 197 from the array station 95. The secondary well plate is sealed 199, the primary master plate is re-lidded 201 and the barcodes of these plates are re-scanned and storage unit location is assigned 203. LIMS 24 marries the master plate to transportation apparatus location 204. The secondary well plates are then moved to freezer 205. The secondary well plates that contain DNA samples, and optionally the morphology control sequences, is sealed with a barrier seal. The barrier seal will prevent sample degradation and provide a safe storage mechanism. The transportation storage unit that houses the secondary well plates after processing has a specific number as well as specific locations within the unit. Each location inside the unit has an associated unique barcode number. Each secondary well plate that is removed from the workstation 14 will have it barcode scanned, as well as a scanning of the barcode of a specific location within the transportation storage unit. LIMS 24 records the secondary well plate number as well as its specific location. The marrying of the secondary well plate with its location is useful if a sample needs to be re-accessed 204. The transportation storage unit will be moved to a cold storage room for long-term storage.

Hybridization Station 96

The substrate 229 is placed in a heating cassette 177 for hybridization. Now referring to FIG. 9, a heating cassette 220 is shown, by way of example. This heating cassette 220 is made of a beveled top 225, a plurality of spacers 226, a metal frame 227 and tension clamps 230. The substrate 229 is lowered into the metal frame 227 and plastic spacers 226 are placed on top of the substrate 229 running lengthwise along the edge. The beveled top plate 225 is then lowered on around of the substrate 229 only separated by the plurality of spacers 226. The metal tension clamps 230 are then applied to the heating cassette 220, which hold the cassette 220 together securely. The barcode of the substrate 231 will extend beyond the heating cassette 220 to facilitate scanning.

Now referring to FIG. 7C, in the preferred embodiment, the heating cassette 220 is assembled 178. The substrates 229 in the heating cassettes 220 are transferred 179 to the heating block (Gene Paint®—Tecan) (Raleigh-Durham, N.C.). The function of the heating block is to increase and decrease temperature. In the preferred embodiment, the heating block is heated to 95–99° C. for two minutes in order to separate the double stranded DNA making it more amenable to hybridization 181. The substrate 229 is then washed with 10 to 20 volumes of ethanol 115. In the preferred embodiment, the substrate 229 is then dried by forcing compressed $N_2$ into the top bevel of the heating cassette forcing out any residual ethanol. A sufficient amount of Casine, bovine serum albumine (BSA) or any commercial available blocking agent is dispensed 183 to the bevel of the heating cassette 220 to block unbound surface chemistry, i.e. aldehydes. The heating cassette 230 is incubated 184 on the heating block. Following the blocking of the surface chemistry with the blocking agent, the substrate 229 is washed 185. In the preferred embodiment, the substrate 229 is wash with de-ionized water for one minute three different times.

The genomic DNA, which is immobilized on the substrate 229, is hybridized 187 with the probes. The LIMS 24 directs the Hybridization Station 96 to dispense reagents, such as probes, as selected by the remote user 1 in the Survey of Work 23. In the preferred embodiment, various probes are added to each DNA spot on the substrate 229. The spot can be the sample to be tested or the spot can be the corresponding control sample of DNA. The first probe is specific for a portion of the designated genetic sequence, which for both transgenic and targeted mutagenesis screening, is referred to as the target genetic sequence 63. The target probe specific for the target genetic sequence is referred to as a target binding probe.

In the preferred embodiment, additionally, at least one second probe specific for a portion of the reference genetic sequence is added to the hybridization buffer. This probe can be referred to as a reference binding probe. The function of the reference binding probe is to provide a designated quality control checkpoint. The reference binding probe has a genetic sequence that is complementary to the gene or gene segment in the species being screened, i.e. the reference genetic sequence.

The endogenous gene used as a reference genetic sequence will have a reiteration frequency similar to that of the transgene, so that the similar amount of hybridizations and linear curves will be obtained with each probe. Individuals carrying 1–10 copies of a transgene, any single copy mouse gene can be used as the reference genetic sequence. Examples, of a single copy mouse gene present in the species *Mus* are shown in the Table 1.

TABLE 1

| 32.MMHAP9FLC5.seq.53F | ATCACAAGTACTGGGAGAGG (SEQ ID NO:6) |
|---|---|
| MHAa67g1.seq.120F | GTCTCAGAGGTTAACTCACC (SEQ ID NO:7) |
| D9Mit211.1.38 | TTCTTATCTTCAGCCCCACC (SEQ ID NO:8) |

TABLE 1-continued

| X61434.129F | ATAACACGGTGTGCACCACG (SEQ ID NO:9) |
|---|---|
| U11075.95F | TCCCTTCCTGTTGACTACAG (SEQ ID NO:10) |
| Z49987.38F | TACCCACACGGGCTTAAAAC (SEQ ID NO:11) |
| 32.MMHAP9FLC5.seq.53R | CACTGCCAGTGTGTTTTCAC (SEQ ID NO:12) |

Additionally, for example, the mouse Major Urinary Protein gene family include 20–30 copies per haploid genome. The gene sequences included in the major protein family include:

Mup_ctgtgacgtatgatggattcaataca (SEQ ID NO: 13).
mup tcggccatagagctccatcagctgga (SEQ ID NO: 14).
mup ctgtatggataggaagggatgatgc (SEQ ID NO: 15).
mup ggctcaggccattcttcattctcgggcct (SEQ ID N: 16).

To evaluate individuals that contain numerous numbers of transgene integration events, a probe for a ribosomal RNA gene works well. Ribosomal RNA gene can adequately elucidate 50 to several hundred copies. Hogan, B., Beddington, R., Constantini, F. and Lacy, E. (1994) Manipulating the Mouse Embryo, $2^{nd}$ ed. Cold Springs Harbor Laboratory Press, Cold Springs Harbor, N.Y. (hereby incorporated by reference.)

In addition to the target binding probe, and the reference binding probe, the morphology binding probe can be added to the hybridization buffer. The function of the morphology binding probe is to provide a quality control checkpoint to ensure that the printing process is successful. This quality control allows for the determination of whether a target sample was applied to the substrate. Also, it allows for the shape of the deposited sample to be evaluated in order to evaluate reproducibility across samples and substrates.

Once the target binding probe, reference binding probes, and optionally morphology binding probe are suspended in hybridization buffer the probe amplification molecules or secondary signal generation reagent is also added to the mixture. The amplification molecules such as a dendrite probe, has a nucleic acid capture sequence that is complementary to the target binding probe, morphology binding probe or reference binding probes. Alternatively, the epitome of the target binding probe, morphology binding probe and reference binding probes may be incubated at 45° C. to 50° C. to pre-hybridize the probes with the secondary signal generating reagent.

Different techniques may be employed in order to label the probes. Both direct labeling techniques and indirect labeling provide acceptable results. The indirect methodology as is described in U.S. Pat. Nos. 5,731,158; 5,583,001; 5,196,306 and 5,182,203. In the direct labeling technique the labeled probe hybridizes to the target genetic sequence. The probe will be directly modified to contain at least one fluorescent, radioactive or staining molecule per probe, such as cyanine, horseradish peroxidase (HRP) or any other fluorescent signal generation reagent. The fluorescent signal generation reagent includes, for example, FITC, DTAF and FAM. FAM is a fluorescein bioconjugate made of carboxy-fluorescein succinimidyl ester (e.g. 5-FAM (Molecular Probes, Eugene, Oreg.). DTAF is a fluorescein dichlorotriazine bioconjugate.

The indirect labeling techniques uses a probe that binds the selected genetic target sequence and that has been modified to contain a specified epitome or if it has a nucleic acid binding sequence it forms a bipartite probe. The probes are made based on the remote user's 1 screening parameter selections. The remote user 1 submits the probe sequence 64 that correlates to the target genetic sequence 63. In addition to the target sequence 63, an additional binding sequence beyond the specified target sequence 63 is added. The combination of these two elements gives rise to a bipartite probe.

For example, the binding sequence of the probe may have the same sequence as the 5' end of reverse transcriptase. So the bipartite probe would contain the binding sequence of:

5'CCG GCT GAG TGA CGC GCA GAA GAC AGG GAC G—Probe Sequence 3'. (SEQ ID NO:17). This binding sequence would then be complimentary to the capture sequence for the Cy3 dendrite 5'GGC CGA CTC ACT GCG CGT CTT CTG TCC CGC C-3' (SEQ ID NO:18).

The target genetic sequence 63 is specific for the probe genetic sequence 64 respectively. The binding sequence of the bipartite is free and does not bind to the target genetic sequence 63. In the same manner, with respect to the reference genetic sequence, the reference binding probe sequence is specific for the reference genetic sequence. The binding sequence of the bipartite probe is free and does not bind to the associated genetic sequence. Examples of bipartite probes, complementary to single copy mouse genes, are shown the table below:

TABLE 2

| | | |
|---|---|---|
| AAA.32.MMHAP9FLC5.seq.53f | 5'-GGC CGA CTC ACT GCG CGT CTT CTG TCC CGC CATCACAAGTACTGGGAGAGG | (SEQ ID NO:19) |
| AAAMHAa67g1.seq.120F | 5'-GGC CGA CTC ACT GCG CGT CTT CTG TCC CGC CGTCTCAGAGGTTAACTCACC | (SEQ ID NO:20) |
| AAAD9Mit211.1.38 | 5'-GGC CGA CTC ACT GCG CGT CTT CTG TCC CGC CTTCTTATCTTCAGCCCCACC | (SEQ ID NO:21) |
| AAAX61434.129F | 5'-GGC CGA CTC ACT GCG CGT CTT CTG TCC CGC CATAACACGGTGTGCACCACG | (SEQ ID NO:22) |
| AAAU11075.95F | 5'-GGC CGA CTC ACT GCG CGT CTT CTG TCC CGC CTCCCTTCCTGTTGACTACAG | (SEQ ID NO:23) |
| AAAZ49987.38F | 5'-GGC CGA CTC ACT GCG CGT CTT CTG TCC CGC CTACCCACACGGGCTTAAAAC | (SEQ ID NO:24) |
| AAA32.MMHAP9FLC5. | 5'-GGC CGA CTC ACT GCG CGT CTT CTG TCC CGC CCACTGCCAGTGTGTTTTCAC | (SEQ ID NO:25) |

Examples of bipartite probes, complementary to Mouse Major Urinary Protein are shown in the table below. These bipartite probes are comprised one of the MUP genetic sequences and an second genetic sequence that is complementary to an amplification molecule.

TABLE 3

| | |
|---|---|
| Mup_probe1 5'-GGCCGACTCACTGCGCGTCTTCTGTCCCGCCCTGTGACGTATGATGGATTCAATACA | (SEQ ID NO:26) |
| Mup probe2 5'GGCCGACTCACTGCGCGTCTTCTGTCCCGCCTCGGCCATAGAGCTCCATCAGCTGGA | (SEQ ID NO:27) |
| Mup probe 3 5'-GGCCGACTCACTGCGCGTCTTCTGTCCCGCCCTGTATGGATAGGAAGGGATGATGC | (SEQ ID NO:28) |
| Mup probe4 5'-GGCCGACTCACTGCGCGTCTTCTGTCCCGCCGGCTCAGGCCATTCTTCATTCTCGGGCCT. | (SEQ ID NO:29) |

An amplification molecule, such as a dendrimer or tyramide, is introduced. The amplification molecule is bound directly or indirectly to the nucleic acid binding sequence or epitome. Free bipartite probes and excess amplification molecules are removed via several successive wash steps. The bound amplification molecule emits a signal that has a linear relationship to the number of bound molecule.

Typical modification of binding probes include, but not limited to biotinylation and fluorescein attachments. A secondary signal generation reagents, such as an enzyme, is then bound to the epitome. The secondary signal generation element may have a signal molecule directly attached to it or it may activate or facilitate the attachment of a another signal unit. Multiple signals units may be used to amplify the signal of the target.

Dendrimers, tyramide or the like are examples of amplification molecules that have traditionally been used to amplify cDNA for gene expression analysis and can be used in the present method.

In the preferred embodiment, LIMS 24 directs the hybridization station 96 to direct a liquid dispenser to pipette the selected binding probes and the hybridization buffer. A number of hybridization buffers are acceptable, such as water and saline sodium citrate (SSC). Alternatively, buffer solutions such as 0.25 $NaPO_4$, 4.5% SDS, 1 mMEDTA, 1×SSC or 40% Formamide, 4×SSC, 1% SDS may also be used.

The hybridization solution will then be applied 187 to the bevel top 225 of the heating cassette 220. The substrates 229 in the heating cassette 220 will be incubated 189. In the preferred embodiment, the hybridization mixture is incubated 189 for between 4 to 12 hours at a temperature ranging from 40° C. to 65° C. on the heating block after the target binding probe, reference binding probe and optional morphology binding probe have hybridized to their respective targets. It should be noted that the hybridization solution can contain the amplification molecules or secondary signal reagents or they may be added secondarily.

Once the substrates 229 have been incubated 189 with the hybridization solution the surface of the substrate is washed 191 several times to remove any excess reagent such as probe amplification molecules or secondary signal reagents. In the preferred embodiment, the substrates 229 will first be washed 191 and incubates at 55° C. with several volumes of 2×SSC, 0.2% SDS for ten minutes 189. The substrate will again be washed at room temperature for 10 minutes with several volumes of 2×SSC. The final wash will be conducted at room temperature for ten minutes with 0.2×SSC.

The substrate is dried 197 to facilitate imaging. In the preferred embodiment, the substrate is dried by forcing compress Nitrogen into the top bevel of the heating cassette. The compress Nitrogen drying will continue for several minutes until all of the residual buffer is forced out of the heating cassette and the substrate is dry.

Detection Station 97

This detection station 97 involves detecting the signal from the at least one labeled probe, specific for a portion of said designated genetic sequence at a first and second locations on said substrate, and comparing the signal from the first and second locations on the substrate to detect a designated genetic sequence in the sample of genomic DNA.

In the preferred embodiment, the substrates 229 are then transferred to the detection station 97. The substrates 229 are loaded into a commercially available imaging cassette, such as GSI Lumonics (Watertown, Mass.) and the imaging cassettes are loaded into the microarray imager GSI Lumonics 5000 (Watertown, Mass.) used according to the manufacturer's instructions. The substrates 229 is exposed to an excitatory energy source to produce a quantifiable signal 195 from the signal molecule. More particularly, the substrate's barcode will be scanned and reported 120 to LIMS 24. The substrate surface will be scanned with and at least three different channels and the results will be recorded 120 in LIMS 24. The individual substrates 229 will have their barcodes scanned and married to a storage location barcode. The reference binding probes, the target binding probe and optionally the morphology probe signal will be recorded and analyzed.

Figure 10:
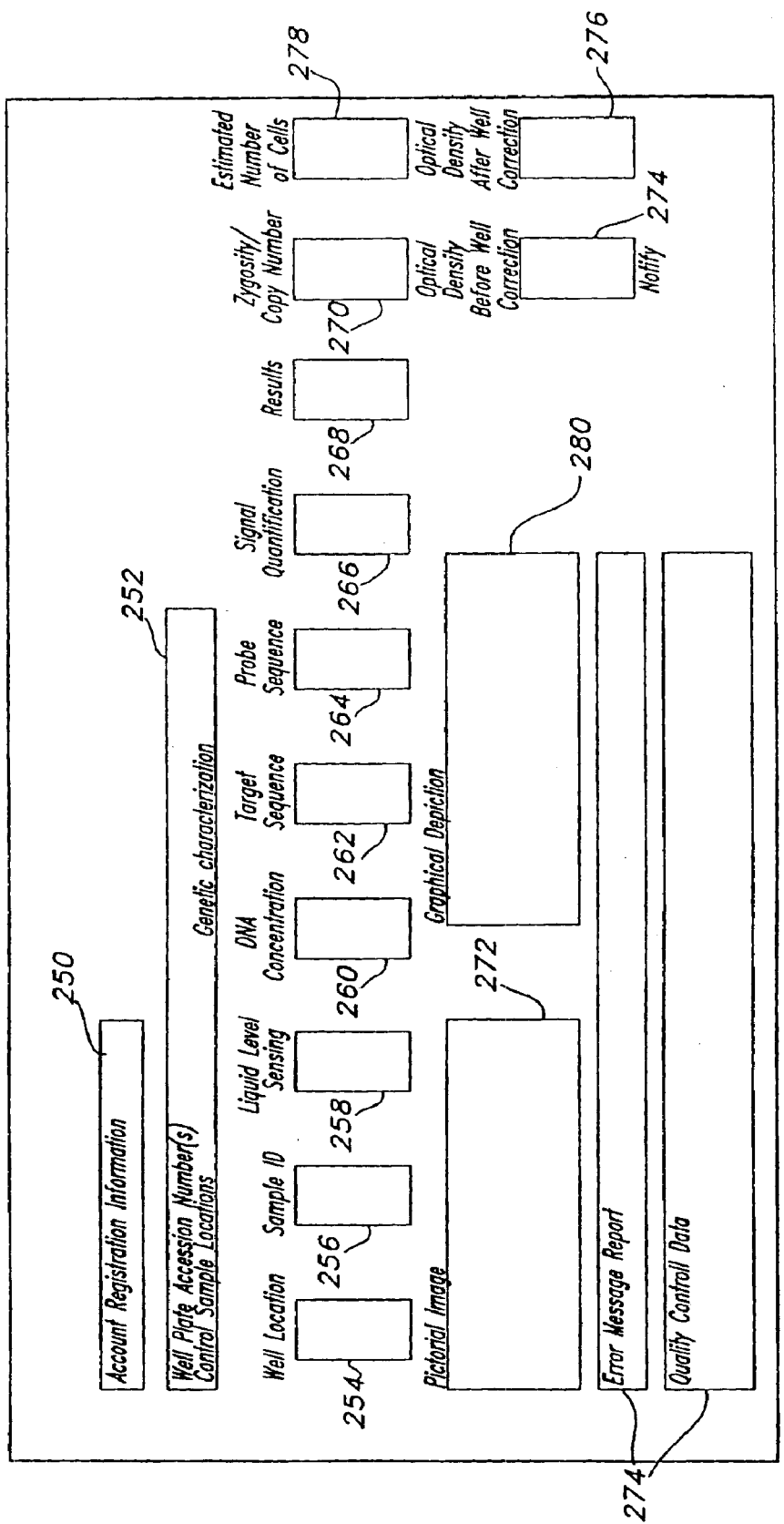
FIG. 10 is a screen display illustrating a document on the transgenic screening laboratory's web site relating to an outcome file.

Now referring to FIG. 10, LIMS 24 now prepares the outcome report 249. Several calculations are performed in LIMS 24 before they are posted to the outcome report 249. In the preferred embodiment, such calculations include the evaluation of all three replicate per sample. The slope of the curve (quantified hybridization intensity/ng DNA) obtained with the target binding probe is divided by the slope of the curve of the designated control probe for each individual sample. This is referred is the induction ratio. The induction ratios are then compared to determine the closeness of the replicates to the control and other replicates induction ratios. Once the induction ratios are calculated the qualitative and quantified results are posted to outcome reports 249. Calculating the linear relationship between the experimental quantified signal and the quantified signals of designated control elucidates the copy number, zygosity or mosaic nature of the sample. The ratio for homozygous individuals should be twice the ratio of heterozygous individuals. Additionally, the cell number is determined from the amount of genomic DNA that is recovered from the isolation process.

Now referring to FIG. 10, the sample outcome report 240 may include account registration 250, well plate accession number(s) 252, control sample locations 250 and genetic characterization of the designated control 252. Additionally, the outcome report 249 may include well location 254, sample identification 256, liquid level sensing 258, DNA concentration 260, target sequence 262, probe sequence 264, signal quantification 266,qualitative results 268, zygosity/copy number 270, optical density reading per well before correction 274, optical density reading after correction 276, estimated number of cells analyzed 278, quantitative analysis via comparison to designated control signal strengths allowing for copy number estimation, zygosity or mosaic nature 270. The outcome report 249 may also include a picture file (email) or pictorial representations of results 272. Additionally, information gathered at the request of the remote user 1 from optimization and sequence confirmation quality control data and error messages will be included in the outcome report 249. The remote user 1 may choose to have this file electronically sent or be electronically notified. Additionally, remote user 1 has the option to have a hard copy sent via the postal service.

Once the LIMS 24 has compiled all the data for the outcome report 249, the outcome report will be sent 7 to the remote user 1. In the preferred embodiment, LIMS 24 will send the report via a remote link 7 to either the remote user 1 or the order manager 22 which can post the results on the web site 16 or via an electronic link 7 send the outcome report 249. The LIMS 24 224 will keep results available for six months and then the results will be recorded onto a long-term storage disk and archived.

In an alternative embodiment, high through put polymerase chain reaction (PCR) or variation of the PCR reaction such as Taqman® (Perkin Elmer, Inc. Wellsley, Mass.) or molecular beacons sold by IDT (Coralville, Iowa) can be used for conducting automated transgenic and targeted mutagenesis screening. The user's account registration, survey of work and sample identification and designation could be created with the same or equivalent factors taken into consideration. Additionally, the supplies, shipping tracking, sample tracking, quality control and results software architecture could be reproduced in a similar mannerism. The modification for the use of a PCR reaction would require the additional information being delineated in the order process, specifically the survey of works. Using this equivalent chemistry would require the user to designate criteria such as the reaction buffer, magnesium concentration, primer sequences, primer concentration, dNTP concentration, cycle conditions and reaction volume. The automated liquid handling could adjust these variables and dispense the reaction buffer to the appropriate location. While tracking the samples through the automated system the genomic DNA may be isolated in an automated fashion via a vacuum manifold isolation, microparticle isolation or chemical extraction. Isolated mammalian DNA can be loaded into a high throughput thermocycler, such as the IAS's Genomatron (Boston, Mass.). Alternatively, substrates such as chemically treated glass, plastic, membrane or any combination could be used as a reaction substrate. These substrates can be housed onto a heating block that heats and cools according the thermal parameters of PCR. The liquid handling platform would add the appropriate reaction buffer to each sample of a well or across the surface of a substrate. The detection of the amplification can be staining via gel electrophoresis or capillary electrophoresis. Detection could also be qualified/quantified by the incorporation of florescent or radiolabeled dNTP's during the PCR reaction or via indirect staining staining methods.

An alternative PCR detection method would include the use of a Taqman® (Perkin Elmer, Inc., Wellsley, Mass.) probe. The Taqman® (Perkin Elmer, Inc., Wellsley, Mass.) probe is composed of a signal generating element (reporter dye) and a quenching element (quenching dye) that under normal conditions does not allow for the detection of the signal-generating element. The oligonucleotide Taqman® (Perkin Elmer, Inc., Wellsley, Mass.) probe sequence is homologous to an internal target sequence present in the PCR amplicon. The specific hybridization reaction of the Taqman® (Perkin Elmer, Inc., Wellsley, Mass.) probe to the amplicon allows the quenching element to be separated from the signal-generating element. The signal molecule that is released is quantifiable. The signal strength is proportional to the number of bound Taqman® (Perkin Elmer, Inc., Wellsley, Mass.) primers.

Akin to the Taqman® (Perkin Elmer, Inc., Wellsley, Mass.) technology is the molecular beacon technology. Molecular beacons can discriminate between single base variances. The probe is equipped with a signal generation element, such as a fluorescent molecule, and a quencher element. Once the probe properly binds to it complimentary sequence the quencher element is removed and the fluorescent molecule is then detectable.

The following examples are provided by way of examples and are not intended to limit the scope of the invention.

EXAMPLES

Example 1

Transgenic Screening

A remote user 1 accesses the web site 19 for the screening laboratory 20 to order testing services. The remote user 1 enters the account number 31 that had previously been specifically assigned by the screening laboratory 20. After the remote user 1 completes the Account Registration 21 the remote user 1 is presented with the Survey of Work Section 23. The first designation that is required by the Survey of Work Section 23 by the remote user 1 is to identify if the samples are of a transgenic or targeted mutagenesis in nature.

The remote user 1, in this example, designates that the samples to be tested are of a transgenic 60 nature. The remote user 1 specifies 62 only one transgenic line is to be tested. The designated genetic sequence 61 to be tested is "HUPPCA." The remote user 1 then specifies 47 transgenic samples needs to be screened from this line 62. The remote user 1 identifies the target genetic sequence to be detected 63. The remote user 1 provides base sequence 64 of the probe is GCA AGG ACG CAA GGA AGC AGA G (SEQ ID NO:30). That is complementary to the target genetic sequence 63. The probe sequence the user indicates is linked to the binding sequence of:
5'-GGC CGA CTC ACT GCG CGT CTT CTG TCC CGC (SEQ ID NO:31)
Which results in the bipartite probe of:
5'-GGC CGA CTC ACT GCG CGT CTT CTG TCC CGC GCA AGG ACG CAA GGA AGC AGA G (SEQ ID NO:32)
This binding sequence specifically couples to the capture arm of the reverse transcriptase sequence for the Cyanine 3 (Cy3) dendrimer.

The remote user 1 is presented with the Sample Identification and Designation screen as shown in FIG. 6. The screen presents an image of the source 96 well plate in the proper orientation. This pictorial representation aids the user in the process of specifically designating each sample into its correct Source 96 well location. Each of the remote user's samples are correlated, recorded and tracked to a specific well of the source plate as shown in FIG. 6.

The remote user 1 loads the source well plate 2 with the proper samples into the correct locations as depicted in FIG. 6. Information about the nature of the designated control is ascertained. This information includes the zygosity and copy number, if known 90. The user reconstitutes the provided lyophilized lysis reagent with de-ionized water. The user pipettes a sufficient amount of lysis buffer 4 into each well of the source well plate 2 to cover the samples. The source well plate 2 is then sealed with a barrier mechanism. To add additional structural integrity, the source well plate 2 is sealed with a rigid lid. The source well plate(s) 2 is loaded into the packing and shipping materials 17 provided. The package is transmitted 16 to the screening laboratory.

The package is received by the screening laboratory 20 and the source well plate(s) 2 are removed and loaded into the work station 14. While all samples are being individual tracked the samples have their genomic DNA extracted and optimized. The quantity of DNA is recorded. The genomic DNA sample and designated control sample are deposited on an optically flat glass slide and hybridized with:
Reference binding probes:
5'-CCG GCT GAG TGA CGC GCA GAA TCA AGG GCG CTTCTTATCTTCAGCCCCACC (SEQ ID NO: 33)
The 5'-CCG GCT GAG TGA CGC GCA GAA TCA AGG GCG element of the bipartite probe specifically binds to the unique capture arm of a Cyanine 5 (Cy5) dendrimer; and Target binding probes:
5'-GGC CGA CTC ACT GCG CGT CTT CTG TCC CGC GCA AGG ACG CAA GGA AGC AGA G (SEQ ID NO:32)

and amplification molecules (Cy3 and Cy5 dendrimers).

An optically flat glass slide is subjected to an excitement energy laser and the quantifiable data is recorded. An outcome report 249 is generated and transmitted over the Internet 7 to the remote user 1. The outcome report 249 contains the account registration information 250, the well plate numbers 252, genetic characterizations 254, well locations, sample identification 256, DNA concentration 260, target sequences 262, probe sequence 264, signal quantification 266, results 268, zygosity/copy number 270, estimated cell number 278, pictorial representation 272, graphical representation 280, error messages 274 and quality control data 274.

Example 2

Targeted Mutagenesis

A remote user 1 accesses the web site 19 for the screening laboratory 20 to order testing services. The remote user 1 enters the account number 31 that had previously been specifically assigned by the screening laboratory 20. After the remote user 1 completes the Account Registration 21 the remote user 1 is presented with the Survey of Work 23. The first designation that is required by the Survey of Work section, by the remote user 1 is to identify if the samples are of a transgenic or targeted mutagenesis in nature.

The remote user 1 in this example designates that the samples to be tested are of a targeted mutagenesis nature 70. The remote user 1 specifies only one 71 knock-out line 72, NSE-PPCA (neuron specific enolase), is to be tested. The designated genetic sequence, which is a knock-out line, to be tested is for the selectable marker hygromycin (SEQ ID NO:2). The remote user 1 then specifies 47 NSE-PPCA samples needs to be screened from this line. The remote user 1 identifies the selectable marker target sequence of hygromycin to be detected 74. The remote user 1 specifically indicates that this selectable marker has not been removed 75 with recombinate technologies, such as Cre-lox or FLP/FRT. The selectable marker target genetic sequence is provided 63. A probe sequence of the hygromycin probe is CAG GAT TTG GGC AAC ATC TT (SEQ ID NO:34) is designated 64. The probe sequence 64 the remote user 1 indicates is linked to the binding sequence of:
5'-GGC CGA CTC ACT GCG CGT CTT CTG TCC CGC (SEQ ID NO:31)

This binding sequence specifically couples to the capture arm of the reverse transcriptase sequence for the Cyanine 3 (Cy3) dendrimer.

The remote user 1 is presented with the Sample Identification and Designation screen. The screen presents is an image of the source well plate 2 in the proper orientation as shown in FIG. 6. This pictorial representation aids the remote user 1 in the process of specifically designating each sample into its correct source well plate 2 location. Each of the remote user's 1 samples are correlated, recorded and tracked to a specific well of the source plate. The user identifies the accession number 3 from the barcode of the Source plate.

The remote user 1 loads the source well plate 2 with the proper samples into the correct locations as designated in FIG. 6 in the sample Identification Section 25. Information about the nature of the designated control is ascertained 90. The remote user 1 reconstitutes the provided lyophilized lysis reagent with de-ionized water. The user pipettes a sufficient amount of lysis buffer 4 into each well of the source plate 2 to cover the samples. The source well plate 2 is then sealed with a barrier mechanism. To add additional structural integrity, the source well plate 2 is sealed with a rigid lid. The source well plate(s) is loaded into the packing and shipping materials provided. The remote user 1 places the shipping package 15 and ships 16 to the screening laboratory 20.

The package 15 is received by the screening laboratory 20 and the source well plate(s) 2 are removed and loaded into the work station 14. While all samples are being individual tracked the samples have their genomic DNA extracted and optimized in an automated fashion. The quantity of DNA is recorded. The DNA is printed onto a substrate and hybridized with reference probes:
5'-CCG GCT GAG TGA CGC GCA GAA TCA AGG GCG CTTCTTATCTTCAGCCCCACC (SEQ ID NO:35)

The 5'-CCG GCT GAG TGA CGC GCA GAA TCA AGG GCG element of the bipartite probe specifically binds to the unique capture arm of a Cyanine 5 (Cy5) dendrimer, and target binding probes:
5'-GGC CGA CTC ACT GCG CGT CTT CTG TCC CGC CAG GAT TTG GGC AAC ATC TT (SEQ ID NO:36)
and amplification molecules (Cy3 and Cy5 dendrimers).

An optically flat glass slide is subjected to an excitement energy laser and the quantifiable data is recorded. An outcome report 249 is generated and transmitted over the Internet 7 to the remote user 1. The outcome report 249 contains the account registration information 250, the well plate numbers 252, genetic characterizations 254, well locations, sample identification 256, DNA concentration 260, target sequences 262, probe sequence 264, signal quantification 266, results 268, zygosity/copy number 270, estimated cell number 278, pictorial representation 272, graphical representation 280, error messages 274 and quality control data 274.

Example 3

Eukaryotic Genomic DNA Magnetic Particle Isolation

Tested with several mouse tails acquired from St. Jude Children's Hospital. Samples were lysed expelling the contents of the cell including the chromosomal DNA. The lysis buffer was made of 4M urea, 0.1 M Tris-HCl (pH~7.5), 180 mM NaCl, 10 mM EDTA, 1% SDS, 5 mM DDT, 415 mg of Proteinase K and Rnase. The samples were incubated in transport at room temperature for 24 hours. The lysate created a solution containing genomic DNA without the cloned DNA elements from prokaryotic work. The genomic DNA was separated. The lysate was combined with carboxyl-terminated iron oxide particles. Polyethylene Glycol (PEG) 8000, 0.02% Sodium Azide, 2.5M NaCl was added and gently mixed. The samples were incubated for ten minutes at room temperature. The samples were exposed to a magnetic field for several minutes until the supernatant cleared. The supernatant was aspirated and discarded. The microparticles were washed and re-suspended with 70% ethanol and 30% de-ionized water to remove any salt. The samples were exposed to the magnetic field until the supernatant was clear. The supernatant was then aspirated and discarded. The ethanol washing was repeated. The microparticles were air dried for several minutes. The microparticles were re-suspended in 0.01M Tris (pH 7.4), 0.02% Sodium Azide. The Tris-microparticle solution was incubated at 80° C. for several minutes. The samples were re-exposed to the magnetic field until the supernatant was clear. The supernatant was aspirated and placed into clean tubes. To determine the recovery yield of genomic DNA, a Picogreen quantification assay was performed. Picogreen (Molecular Probes, Eugene, Oreg.) is a commercially available stain that binds only to double stranded DNA. Samples were loaded into cuvettes and were exited at 480 nm. The fluoresence emission intensity was measured at 520 nm using a spectrofluorometer and plotted as a function of DNA concentration.

TABLE 4

Mouse Tail Tissue Genomic DNA

| | |
|---|---|
| 1A | 450 ng |
| 1B | 430 ng |
| 2 | 584 ng |
| 3 | 2070 ng |
| 4 | 1944 ng |

The results show that mammal genomic DNA in tissue or cells is successfully lysed at room temperature and genomic DNA is recovered with magnetic particles.

Example 4

Immobilization, Hybridization, Detection of Mammalian Genomic DNA

To evaluate the difference and to determine the optimal conditions for which mouse genomic DNA can be bound to a substrate, hybridized to a probe and have quantifiable signal detected several iterations were conducted. There were two distinct types of mouse genomic DNA that was under study, sonicated and unsonicated. Both of these types of mouse genomic DNA were used to make serial dilutions in four different buffers. There were six serial dilutions of both mouse genomic DNA's made ranging from 538 ng/μL to 17 ng/μL. There were seven endogenous gene sequences that are ubiquitous to all species of mice that were amplified with PCR to serve as designated controls.

Seven mouse markers that naturally occur in the mouse genome were amplified using PCR. These markers function as controls for the unknown stock genomic DNA. The markers were:

TABLE 5

| | | |
|---|---|---|
| 32.MMHAP9FLC5.seq.53F | ATCACAAGTACTGGGAGAGG | (SEQ ID NO:6) |
| MHAa67g1.seq.120F | GTCTCAGAGGTTAACTCACC | (SEQ ID NO:7) |
| D9Mit211.1.38 | TTCTTATCTTCAGCCCCACC | (SEQ ID NO:8) |
| X61434.129F | ATAACACGGTGTGCACCACG | (SEQ ID NO:9) |
| U11075.95F | TCCCTTCCTGTTGACTACAG | (SEQ ID NO:10) |
| Z49987.38F | TACCCACACGGGCTTAAAAC | (SEQ ID NO:11) |
| 32.MMHAP9FLC5.seq.53R | CACTGCCAGTGTGTTTTCAC | (SEQ ID NO:12) |

The PCR fragments were separated on an agarose gel and the amplicons were isolated with using magnetic particles using the procedure set out in Hawkins '628 patent. A quantification analysis (Picogreen, Molecular Probes, Eugene, Oreg.) was employed to determine the specific concentration of PCR amplicon DNA. Serial dilutions of the known concentrations of PCR Amplicon controls and serial dilutions of both sonicated and un-sonicated stock endogenous mouse genomic DNA was printed onto the substrates. The amplicon (generic name for portion of genetic sequence that is amplified DNA and the genomic DNA were fixed to the substrates via covalent and/or non-covalent linkage.

TABLE 6

Results from the quantification of controls:

| well # | gel lane | PG5_raw | PG5, ng/μl | ng yield | ug yield | Amplicon |
|---|---|---|---|---|---|---|
| A1 | 1 | 0 | 0.020434 | | | |
| A2 | 3 | 51.6 | 6.2 | 2976 | 2.98 | U11075.95 |
| A3 | 5 | 26.0 | 3.1 | 1502 | 1.50 | q.120F |
| A4 | 7 | 33.6 | 4.0 | 1940 | 1.94 | D9Mi211.1.38 47.mmhap5flh |
| A5 | 9 | 20.3 | 2.5 | 1177 | 1.18 | 5.seq.85 |
| A6 | 11 | 28.5 | 3.4 | 1648 | 1.65 | LC5.seq.53F |
| A7 | 13 | 22.5 | 2.7 | 1305 | 1.31 | Z49987.38F |
| A8 | 15 | 11.2 | 1.4 | 655 | 0.65 | X61434.129F |
| A9 | 17 | 15.4 | 1.9 | 894 | 0.89 | Actb-pA |

Results of the Control Genomic DNA Signal Serial Dilution

PCR amplicons printed onto substrates, probed, and detected is well documented in the literature. PCR amplicons are generally used for gene expression work. These PCR amplicon controls were made into six serial dilutions in the four different buffers at a concentration gradient that was equivalent to the concentration gradient of the mouse genomic DNA's (538 ng/μL to 17 ng/μL). The sonicated and unsonicated mouse genomic DNA serial dilutions as well as the PCR amplicon control serial dilutions were printed together onto six different types substrates. These substrates were probed with two different types of probes. The FAM probes (direct labeling) and the bipartite probe that was amplified with a dendrimer.

A well-plate holding the serial dilutions was created as follows:

Both the sonicated and unsonicated eukaryotic and prokaryotic DNA was suspended at different concentrations in 4 different buffers. The four buffers include 3×SSC, 50% DMSO, 5.5M NaSCN, and the fourth buffer is the commercially available Tel-Chem (Sunnyvale, Calif.) printing buffer. The mouse genomic DNA was diluted in half 6 times (538 ng/μL, 269 ng/μL, 135 ng/μL, 68 ng/μL, 34 ng/μL and 17 ng/μL). The PCR control serial dilutions were also created. The control dilutions were made from the PCR-amplicons of endogenous mouse genes that were previously amplified. The PCR controls were generated as follows: the first four control serial dilutions were made with 3×SSC buffer, 5.5M NaSCN, 50% DMSO and the Tel-Chem (Sunnyvale, Calif.) commercially available buffer. The beginning concentration of the PCR amplicon DNA was 538 ng/μL. There were 6 dilutions of the PCR amplicons (538 ng/μL, 269 ng/μL, 135 ng/μL, 68 ng/μL, 34 ng/μL and 17 ng/μL). The $5^{th}$ and $6^{th}$ controls were also diluted in a separate well-plate with starting amount 538 ng/μL. Again they were suspended in 3×SSC, 5.5M NaSCn, 50% DMSO as well as the Tel-Chem (Sunnyvale, Calif.) commercially-available buffer.

TABLE 7

384 Well Plate Design

| Mouse genomic sonicated | 3xssc 50% DMSO 5.5 M NaSCN Telechem | Mouse genomic sonicated | 3xssc 50% DMSO 5.5 M NaSCN Telechem | Control #1 Control #2 Control #3 Control #4 | 3X SSC | Control #1 Control #2 Control #3 Control #4 | 5.5 M NaSCN |
| Mouse genomic sonicated | 3xssc 50% DMSO 5.5 M NaSCN Telechem | Mouse genomic sonicated | 3xssc 50% DMSO 5.5 M NaSCN Telechem | Control #1 Control #2 Control #3 Control #4 | 50% DMSO | Control #1 Control #2 Control #3 Control #4 | Telechem |
| Mouse genomic unsonicated | 3xssc 50% DMSO 5.5 M NaSCN Telechem | Mouse genomic unsonicated | 3xssc 50% DMSO 5.5 M NaSCN Telechem | Control #5 Control #6 Control #7 Control #8 | 3X SSC | Control #5 Control #6 Control #7 Control #8 | Telechem |

The following bipartite probes were used:

TABLE 8

| | | |
|---|---|---|
| AAA32.MMHAP9FLC5.seq.53F | 5'-GGC CGA CTC ACT GCG CGT CTT CTG TCC CGC CATCACAAGTACTGGGAGAGG | (SEQ ID NO:19) |
| AAAMHAa67g1.seq.120F | 5'-GGC CGA CTC ACT GCG CGT CTT CTG TCC CGC CGTCTCAGAGGTTAACTCACC | (SEQ ID NO:20) |
| AAAD9Mit211.1.38 | 5'-GGC CGA CTC ACT GCG CGT CTT CTG TCC CGC CTTCTTATCTTCAGCCCCACC | (SEQ ID NO:21) |
| AAAX61434.129F | 5'-GGC CGA CTC ACT GCG CGT CTT CTG TCC CGC CATAACACGGTGTGCACCACG | (SEQ ID NO:22) |
| AAAU11075.95F | 5'-GGC CGA CTC ACT GCG CGT CTT CTG TCC CGC CTCCCTTCCTGTTGACTACAG | (SEQ ID NO:23) |
| AAAZ49987.38F | 5'-GGC CGA CTC ACT GCG CGT CTT CTG TCC CGC CTACCCACACGGGCTTAAAAC | (SEQ ID NO:24) |
| AAA32.MMHAP9FLC5.seq.53R | 5'-GGC CGA CTC ACT GCG CGT CTT CTG TCC CGC CCACTGCCAGTGTGTTTTCAC | (SEQ ID NO:25) |

The FAM modified probes (direct labeling) were used:

TABLE 9

| | |
|---|---|
| CCC32.MMHAP9FLC5.seq.53F | ATCACAAGTACTGGGAGAGG (SEQ ID NO:37) |
| CCCMHAa67g1.seq.120F | GTCTCAGAGGTTAACTCACC (SEQ ID NO:38) |
| CCCD9Mit211.1.38 | TTCTTATCTTCAGCCCCACC (SEQ ID NO:39) |
| CCCX61434.129F | ATAACACGGTGTGCACCACG (SEQ ID NO:40) |

Sonication of Mouse Genomic DNA:

The mouse genomic DNA was sonicated for five minutes with a fixed setting using a horn sonicator.

Array Design:

The array design was as follows: there were six pallets which each held 14 slides for the array machine. Each pellet held one format of slides with exception of the right upper quadrant. Each pallet held 1 format of slides. The left upper quadrant pallet held 14 super-aldehyde slides. The middle upper quadrant pallet held 14 Schliecher Schuell (Dassel, Germany) slides. The right upper quadrant held 5 sigma slides as well as 9 super-amine slides. The lower left quadrant held 14 super-amine slides. The middle lower quadrant held poly-lysine slides and the right lower quadrant held the amino-sylinated slides (SCA slides).

The 384 well-plate was loaded on to the array machine. The array machine was calibrated to accurately deposit the correct amount of sample onto each substrate using a split-pin tip. The array machine plated the contents of the 384 well-plate across the 84 slides. This process took approximately 40 minutes to complete the entire printing. After printing, the Fast Slides® from Schliecher Schuell (Dassel, Germany) were removed because the nitrocellulose membrane was damaged.

Crosslinking the DNA:

These slides were UV cross-linked at 1200 $\mu$J, with the exception of the aldehyde slides. All slides were boiled for 5 minutes to separate the double-stranded DNA on the surface of the substrate. The boiling of the substrates occurred in a slide holder and water. After the substrates were boiled in water for 5 minutes they were dunked into a 100% ethanol for 1 minute, which facilitated the drying of the slides.

The FAM probes were re-suspended, making stock solutions of each probe type. 279 mM/279 μL equals 1 μM. Each stock was 1 μM.

The direct-labeled FAM probes were all combined (multiplexed) into one hybridization buffer. This hybridization buffer was applied across different substrates. 1 μM of the probe or 0.3 pM in 30 μL. The hybridization buffer was created as follows: Approx. 30 μL of solution were needed per substrate. The total volume of hybridization buffer was 180 μL. This hybridization buffer includes 18 μL of 20×SSC, 0.2 μL of probe-one, 0.2 μL of probe-two, 0.2 μL of probe-three, 0.2 μL of probe-four, 1.2 μL of 10% SDS, 6 μL of BSA, and 154 μL of water, equaling a total of 180 μL of buffer. It should be noted FAM traditionally has a high background and low signal. The FAM hybridization buffer was spun for seconds in a microfuge tube after being vortexed for a few brief seconds to ensure proper mixing. The FAM cocktail was applied to the superamine slide 012320, the polylysine slide 012370, the sigma slide 012800, the superaldehyde substrate 012850 and the CSA substrate of 012440. 30 μL of hybridization buffer was applied to the slides. The substrates with the hybridization buffer was then covered with a coverslip from Schliecher Schuell (Dassel, Germany) and were manipulated to remove any air bubbles from under the slide cover that could result in poor hybridization. The substrates were placed in the hybridization chamber with moistened towelettes to ensure that the slides do not dry out. The chambers were placed in a 45.1° C. incubator for 30 minutes. Bovine serum albumin (BSA) was used to adequately blind the chemical groups on the substrate surface. After the hybridization process was completed the slides were washed in 2×SSC with 1%SDS for approximately 5 minutes. The slides were washed for another 5 minutes in 2×SSC. The slides were then washed in 0.6SSC for 5 minutes, followed by a wash in 100% ethanol. The FAM slides were imaged seven day after probing and a detectable signal was quantifiable.

In the preferred embodiment, the bipartite probes as shown in Table 7 were all combined (multiplexed) into one hybridization buffer. This hybridization buffer was applied across the different substrates and incubated. The Cyanine 3 (Cy3) dendrimer was then used to bind to the probe. Now referring to FIG. 11, the Y axis 282 shows the intensity of fluorescence of the labeled prove and the X axis 284 is the sample identification slide. The data from one slide was used to create a graphical representation of the results shown as FIG. 11. The slides were scanned and the quantifiable data was recorded. FIG. 11 shows that genomic DNA can be detected using a microarray imager.

More specifically, the results are shown in Table 10.

TABLE 10

Sonicated and Unsonicated Mouse Genomic DNA Quantified Results Relative to PCR Controls

| Mouse Genome Sonicated 3xSSC Cy3 Dens-Levels | Well Inserted | PCR Control #1 3xSSC Cy3 Dens-Levels | Well Inserted | Mouse Genome Un-Sonicated 3xSSC Cy3 Dens-Levels | Well Inserted | PCR Control #5 3xSSC Cy3 Dens-Levels | Well Inserted |
|---|---|---|---|---|---|---|---|
| 1608.88 | A01 | 913.87 | A13 | 12717 | I01 | 1029.33 | I13 |
| 1829.92 | A01 | 1418.65 | A13 | 15406.2 | I01 | 532.73 | I13 |
| 10838.3 | A02 | 1442.54 | A14 | 27048.1 | I02 | 1165.44 | I14 |
| 17623.8 | A02 | 1683.92 | A14 | 24489.3 | I02 | 1499.83 | I14 |
| 1499.88 | A03 | 971.92 | A15 | 14616.8 | I03 | 513.25 | I15 |
| 1346.29 | A03 | 781.81 | A15 | 19646.3 | I03 | 868.75 | I15 |
| 694.9 | A04 | 637.83 | A16 | 1207.77 | I04 | 595.54 | I16 |
| 1481.81 | A04 | 496.44 | A16 | 999.29 | I04 | 468.33 | I16 |
| 5819.92 | A05 | 741.6 | A17 | 9708.62 | I05 | 738.31 | I17 |
| 6805.9 | A05 | 1056.92 | A17 | 9224.71 | I05 | 607.25 | I17 |
| 1481.29 | A06 | 719.58 | A18 | 745.94 | I06 | 1118.46 | I18 |
| 1629.08 | A06 | 1244.08 | A18 | 1431.6 | I06 | 891.85 | I18 |
| 11949.7 | A07 | 32821.2 | A19 | 6173.75 | I07 | 14934.1 | I19 |
| 9454.98 | A07 | 34354.4 | A19 | 6054.54 | I07 | 15255.2 | I19 |
| 16005.6 | A08 | 12853.5 | A20 | 23767.1 | I08 | 33108.4 | I20 |
| 21630 | A08 | 4668.19 | A20 | 17812.3 | I08 | 31512.9 | I20 |
| 11463.3 | A09 | 1513.67 | A21 | 3185.6 | I09 | 18818.8 | I21 |
| 10900.2 | A09 | 1343.58 | A21 | 3039.54 | I09 | 22902.9 | I21 |
| 4657.04 | A10 | 4713.79 | A22 | 3636.42 | I10 | 15394.6 | I22 |
| 5670.4 | A10 | 2990.83 | A22 | 4685.83 | I10 | 24232.1 | I22 |
| 10906.7 | A11 | 633.38 | A23 | 8357.56 | I11 | 1493.71 | I23 |
| 9271.25 | A11 | 805.77 | A23 | 5246.52 | I11 | 13973.6 | I23 |
| 713.48 | A12 | 1075.42 | A24 | 1381.31 | I12 | 14037 | I24 |
| 738.46 | A12 | 904.88 | A24 | 2326.31 | I12 | 16366.9 | I24 |

The results show that either sonicated or unsonicated genomic DNA can produce a reportable signal when affixed to an optically flat substrate and read with a microarray imager.

Although the present invention has been described and illustrated with respect to preferred embodiments and a preferred use thereof, it is not to be so limited since modifications and changes can be made therein which are within the full scope of the invention.

We claim:

1. In a method for detecting a designated genetic sequence in a sample of murine genomic DNA, obtained from a lysed tissue sample, in a solid phase hybridization assay including a bipartite probe specific for a portion of said murine genomic DNA, the improvement comprising:
    separating said murine genomic DNA from said lysed tissue sample using magnetic particles and immobilizing said murine genomic DNA on to a solid phase, wherein said bipartite probe has a first region specific for a portion of said murine genomic DNA and a second region that binds to a signal emitting dendrimer.

2. The method of claim 1 wherein said signal emitting dendrimer is cyanine 3.

3. The method of claim 1 wherein said probe specific for a portion of said murine genonlic DNA is selected from the group consisting of: SEQ ID NO. 19, SEQ ID NO. 20, SEQ ID NO. 21, SEQ ID NO. 22, SEQ ID NO. 23, SEQ ID NO. 24, and SEQ ID NO. 25.

4. The method of claim 1 wherein said murine genomic DNA concentration is about 12.5 to 500 ng/µL.

5. The method of claim 1 wherein the murine genomic DNA concentration is 17 ng to 250 ng/µL.

6. The method of claim 1 wherein said solid phase is an optically flat substrate.

7. The method of claim 6 wherein said optically flat substrate is glass.

* * * * *